US012376926B2

(12) United States Patent
Wallace et al.

(10) Patent No.: US 12,376,926 B2
(45) Date of Patent: Aug. 5, 2025

(54) SYSTEMS AND INSTRUMENTS FOR TISSUE SEALING

(71) Applicant: Auris Health, Inc., Redwood City, CA (US)

(72) Inventors: Daniel T. Wallace, Santa Cruz, CA (US); Benjamin L. Smith, Sunnyvale, CA (US); Travis R. Marsot, Mountain View, CA (US)

(73) Assignee: CILAG GMBH INTERNATIONAL, Zug (CH)

( * ) Notice: Subject to any disclaimer, the term of this patent is extended or adjusted under 35 U.S.C. 154(b) by 157 days.

(21) Appl. No.: 18/109,151

(22) Filed: Feb. 13, 2023

(65) Prior Publication Data
US 2023/0190395 A1 Jun. 22, 2023

Related U.S. Application Data

(62) Division of application No. 16/563,480, filed on Sep. 6, 2019, now Pat. No. 11,576,738.
(Continued)

(51) Int. Cl.
*A61B 34/30* (2016.01)
*A61B 17/34* (2006.01)
(Continued)

(52) U.S. Cl.
CPC .......... *A61B 34/35* (2016.02); *A61B 17/3423* (2013.01); *A61B 18/1442* (2013.01);
(Continued)

(58) Field of Classification Search
CPC ......... A61B 34/30; A61B 34/35; A61B 17/34; A61B 17/3403; A61B 17/3423;
(Continued)

(56) References Cited

U.S. PATENT DOCUMENTS 3,763,860 A 10/1973 Clarke
4,040,413 A 8/1977 Ohshiro
(Continued)

FOREIGN PATENT DOCUMENTS

CN 101443069 5/2009
CN 100515347 7/2009
(Continued)

OTHER PUBLICATIONS

International Search Report and Written Opinion received for PCT Application No. PCT/US2019/050041, mailed on Nov. 4, 2019, 7 pages.

*Primary Examiner* — Vi X Nguyen
(74) *Attorney, Agent, or Firm* — Joshua D. Young

(57) ABSTRACT

A robotic system can include a surgical instrument with a wrist including an elongate shaft extending between a proximal end and a distal end, a wrist extending from the distal end of the elongate shaft, and an end effector extending from the wrist. The end effector may include a first jaw and a second jaw, the first and second jaw being moveable between an open position in which ends of the jaws are separated from each other, and a closed position in which the ends of the jaws are closer to each other as compared to the open position. The surgical instrument may also include at least one rotary cutter extending from the wrist and positioned at least partially within a recess formed in a face of the first jaw.

16 Claims, 32 Drawing Sheets

Related U.S. Application Data

(60) Provisional application No. 62/742,855, filed on Oct. 8, 2018.

(51) Int. Cl.
  *A61B 18/14* (2006.01)
  *A61B 34/35* (2016.01)
  *A61B 17/00* (2006.01)
  *A61B 17/32* (2006.01)
  *A61B 18/00* (2006.01)
  *A61B 34/00* (2016.01)

(52) U.S. Cl.
  CPC ............ *A61B 17/00234* (2013.01); *A61B 2017/00477* (2013.01); *A61B 17/320092* (2013.01); *A61B 2018/0063* (2013.01); *A61B 34/25* (2016.02); *A61B 2034/301* (2016.02); *A61B 2034/305* (2016.02)

(58) Field of Classification Search
  CPC .......... A61B 17/320092; A61B 19/203; A61B 19/5244; A61B 2034/305; A61B 18/14
  See application file for complete search history.

(56) References Cited

U.S. PATENT DOCUMENTS

| | | |
|---|---|---|
| 4,198,960 A | 4/1980 | Utsugi |
| 4,470,407 A | 9/1984 | Hussein |
| 4,532,935 A | 8/1985 | Wang et al. |
| 4,685,458 A | 8/1987 | Leckrone |
| 4,747,405 A | 5/1988 | Leckrone |
| 4,854,301 A | 8/1989 | Nakajima |
| 4,854,808 A | 8/1989 | Bruno |
| 4,898,574 A | 2/1990 | Uchiyama et al. |
| 4,983,165 A | 1/1991 | Loiterman |
| 5,029,574 A | 7/1991 | Shimamura et al. |
| 5,085,659 A | 2/1992 | Rydell |
| 5,196,023 A | 3/1993 | Martin |
| 5,217,465 A | 6/1993 | Steppe |
| 5,308,323 A | 5/1994 | Sogawa et al. |
| 5,318,589 A | 6/1994 | Lichtman |
| 5,325,848 A | 7/1994 | Adams et al. |
| 5,342,381 A | 8/1994 | Tidemand |
| 5,344,395 A | 9/1994 | Whalen et al. |
| 5,353,783 A | 10/1994 | Nakao et al. |
| 5,370,609 A | 12/1994 | Drasler et al. |
| 5,372,124 A | 12/1994 | Takayama et al. |
| 5,411,016 A | 5/1995 | Kume |
| 5,431,649 A | 7/1995 | Mulier et al. |
| 5,441,485 A | 8/1995 | Peters |
| 5,449,356 A | 9/1995 | Walbrink |
| 5,450,843 A | 9/1995 | Moll et al. |
| 5,456,684 A | 10/1995 | Schmidt |
| 5,472,426 A | 12/1995 | Bonati et al. |
| 5,496,267 A | 3/1996 | Drasler |
| 5,501,667 A | 3/1996 | Verduin, Jr. |
| 5,520,684 A | 5/1996 | Imran |
| 5,545,170 A | 8/1996 | Hart |
| 5,562,239 A | 10/1996 | Boiarski et al. |
| 5,562,648 A | 10/1996 | Peterson |
| 5,562,678 A | 10/1996 | Booker |
| 5,572,999 A | 11/1996 | Funda et al. |
| 5,573,535 A | 11/1996 | Viklund |
| 5,613,973 A | 3/1997 | Jackson et al. |
| 5,645,083 A | 7/1997 | Essig et al. |
| 5,653,374 A | 8/1997 | Young et al. |
| 5,658,311 A | 8/1997 | Baden |
| 5,695,500 A | 12/1997 | Taylor et al. |
| 5,697,949 A | 12/1997 | Giurtino et al. |
| 5,710,870 A | 1/1998 | Ohm |
| 5,716,325 A | 2/1998 | Bonutti |
| 5,788,667 A | 8/1998 | Stoller |
| 5,792,165 A | 8/1998 | Klieman |
| 5,797,900 A | 8/1998 | Madhani |
| 5,810,770 A | 9/1998 | Chin et al. |
| 5,893,869 A | 4/1999 | Barnhart |
| 5,897,491 A | 4/1999 | Kastenbauer et al. |
| 5,924,175 A | 7/1999 | Lippitt |
| 5,989,230 A | 11/1999 | Frassica |
| 6,071,281 A | 6/2000 | Burnside et al. |
| 6,093,157 A | 7/2000 | Chandrasekaran |
| 6,110,171 A | 8/2000 | Rydell |
| 6,120,476 A | 9/2000 | Fung et al. |
| 6,120,498 A | 9/2000 | Jani et al. |
| 6,156,030 A | 12/2000 | Neev |
| 6,174,318 B1 | 1/2001 | Bates et al. |
| 6,206,903 B1 | 3/2001 | Ramans |
| 6,183,435 B1 | 6/2001 | Bumbalough et al. |
| 6,251,120 B1 | 6/2001 | Dorn |
| 6,322,557 B1 | 11/2001 | Nikolaevich |
| 6,375,635 B1 | 4/2002 | Moutafis |
| 6,394,998 B1 | 5/2002 | Wallace et al. |
| 6,405,078 B1 | 6/2002 | Moaddeb et al. |
| 6,440,061 B1 | 8/2002 | Wenner et al. |
| 6,508,823 B1 | 1/2003 | Gonon |
| 6,522,906 B1 | 2/2003 | Salisbury et al. |
| 6,577,891 B1 | 6/2003 | Jaross et al. |
| 6,676,668 B2 | 1/2004 | Mercereau et al. |
| 6,685,698 B2 | 2/2004 | Morley et al. |
| 6,706,050 B1 | 3/2004 | Giannadakis |
| 6,817,974 B2 | 11/2004 | Cooper et al. |
| 6,840,938 B1 | 1/2005 | Morley et al. |
| 6,840,948 B2 | 1/2005 | Albrecht et al. |
| 6,994,708 B2 | 2/2006 | Manzo |
| 7,121,781 B2 | 10/2006 | Sanchez |
| 7,250,028 B2 | 7/2007 | Julian et al. |
| 7,282,055 B2 | 10/2007 | Tsuruta |
| 7,306,597 B2 | 12/2007 | Manzo |
| 7,320,700 B2 | 1/2008 | Cooper et al. |
| 7,367,973 B2 | 5/2008 | Manzo et al. |
| 7,422,592 B2 | 9/2008 | Morley et al. |
| 7,559,934 B2 | 7/2009 | Teague et al. |
| 7,736,356 B2 | 6/2010 | Cooper et al. |
| 7,862,580 B2 | 1/2011 | Cooper et al. |
| 7,942,868 B2 | 5/2011 | Cooper |
| 7,963,911 B2 | 6/2011 | Turliuc |
| 7,987,046 B1 | 7/2011 | Peterman |
| 8,002,713 B2 | 8/2011 | Heske |
| 8,038,598 B2 | 10/2011 | Khachi |
| 8,092,397 B2 | 1/2012 | Wallace et al. |
| 8,142,421 B2 | 3/2012 | Cooper et al. |
| 8,187,173 B2 | 5/2012 | Miyoshi |
| 8,257,303 B2 | 9/2012 | Moll et al. |
| 8,337,521 B2 | 12/2012 | Cooper et al. |
| 8,480,595 B2 | 7/2013 | Speeg |
| 8,523,762 B2 | 9/2013 | Miyamoto et al. |
| 8,540,748 B2 | 9/2013 | Murphy et al. |
| 8,578,810 B2 | 11/2013 | Donhowe |
| 8,679,099 B2 | 3/2014 | Cooper et al. |
| 8,690,908 B2 | 4/2014 | Cooper et al. |
| 8,771,270 B2 | 7/2014 | Burbank |
| 8,790,243 B2 | 7/2014 | Cooper et al. |
| 8,820,603 B2 | 9/2014 | Shelton et al. |
| 8,858,547 B2 | 10/2014 | Brogna |
| 8,870,900 B2 | 10/2014 | Julian et al. |
| 8,870,902 B2 | 10/2014 | Deodhar et al. |
| 8,870,912 B2 | 10/2014 | Brisson et al. |
| 8,882,660 B2 | 11/2014 | Phee et al. |
| 8,887,595 B2 | 11/2014 | Williams |
| 8,911,428 B2 | 12/2014 | Cooper et al. |
| 8,945,163 B2 | 2/2015 | Voegele et al. |
| 8,945,174 B2 | 2/2015 | Blumenkranz |
| 8,956,280 B2 | 2/2015 | Eversull et al. |
| 8,991,678 B2 | 3/2015 | Wellman et al. |
| 9,005,112 B2 | 4/2015 | Hasser et al. |
| 9,055,961 B2 | 6/2015 | Manzo et al. |
| 9,095,317 B2 | 8/2015 | Cooper et al. |
| 9,161,771 B2 | 10/2015 | Steger |
| 9,226,761 B2 | 1/2016 | Burbank |
| 9,265,567 B2 | 2/2016 | Orban et al. |
| 9,345,456 B2 | 5/2016 | Tsonton et al. |
| 9,456,839 B2 | 10/2016 | Cooper |
| 9,460,536 B2 | 10/2016 | Hasegawa et al. |

(56) References Cited

U.S. PATENT DOCUMENTS

| | | |
|---|---|---|
| 9,474,569 B2 | 10/2016 | Manzo et al. |
| 9,498,215 B2 | 11/2016 | Duque et al. |
| 9,504,604 B2 | 11/2016 | Alvarez |
| 9,522,003 B2 | 12/2016 | Weir et al. |
| 9,561,083 B2 | 2/2017 | Yu et al. |
| 9,585,641 B2 | 3/2017 | Cooper et al. |
| 9,592,042 B2 | 3/2017 | Titus |
| 9,597,152 B2 | 3/2017 | Schaeffer |
| 9,622,827 B2 | 4/2017 | Yu et al. |
| 9,636,184 B2 | 5/2017 | Lee et al. |
| 9,675,354 B2 | 6/2017 | Weir et al. |
| 9,693,794 B2 | 7/2017 | Manzo |
| 9,713,509 B2 | 7/2017 | Schuh et al. |
| 9,717,486 B2 | 8/2017 | Cooper et al. |
| 9,727,963 B2 | 8/2017 | Mintz et al. |
| 9,730,572 B2 | 8/2017 | Hasser et al. |
| 9,730,719 B2 | 8/2017 | Brisson et al. |
| 9,730,757 B2 | 8/2017 | Brudniok |
| 9,737,371 B2 | 8/2017 | Romo et al. |
| 9,737,373 B2 | 8/2017 | Schuh |
| 9,744,335 B2 | 8/2017 | Jiang |
| 9,757,125 B2 | 9/2017 | Wellman et al. |
| 9,763,741 B2 | 9/2017 | Alvarez et al. |
| 9,788,910 B2 | 10/2017 | Schuh |
| 9,814,530 B2 | 11/2017 | Weir et al. |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,080,576 B2 | 9/2018 | Romo et al. |
| 10,136,959 B2 | 11/2018 | Mintz et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,350,390 B2 | 7/2019 | Moll et al. |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,464,209 B2 | 11/2019 | Ho et al. |
| 10,470,830 B2 | 11/2019 | Hill |
| 10,482,599 B2 | 11/2019 | Mintz et al. |
| 10,493,241 B2 | 12/2019 | Jiang |
| 10,500,001 B2 | 12/2019 | Yu et al. |
| 10,639,114 B2 | 5/2020 | Schuh |
| 10,667,875 B2 | 6/2020 | DeFonzo |
| 10,751,140 B2 * | 8/2020 | Wallace ............... A61B 34/30 |
| 10,765,487 B2 | 9/2020 | Ho |
| 2002/0019644 A1 | 2/2002 | Hastings |
| 2002/0099372 A1 | 7/2002 | Schulze et al. |
| 2002/0111608 A1 | 8/2002 | Baerveldt |
| 2002/0111621 A1 | 8/2002 | Wallace et al. |
| 2003/0004455 A1 | 1/2003 | Kadziauskas |
| 2003/0040681 A1 | 2/2003 | Ng et al. |
| 2003/0065358 A1 | 4/2003 | Frecker |
| 2003/0109877 A1 | 6/2003 | Morley |
| 2003/0109889 A1 | 6/2003 | Mercereau |
| 2003/0158545 A1 | 8/2003 | Hovda et al. |
| 2003/0208189 A1 | 11/2003 | Payman |
| 2004/0143253 A1 | 7/2004 | Vanney |
| 2004/0153093 A1 | 8/2004 | Donovan |
| 2004/0158261 A1 | 8/2004 | Vu |
| 2004/0186349 A1 | 9/2004 | Ewers |
| 2004/0193146 A1 | 9/2004 | Lee et al. |
| 2004/0210116 A1 | 10/2004 | Nakao |
| 2004/0253079 A1 | 12/2004 | Sanchez |
| 2005/0033270 A1 | 2/2005 | Ramans et al. |
| 2005/0054900 A1 | 3/2005 | Mawn |
| 2005/0159645 A1 | 7/2005 | Bertolero |
| 2005/0240178 A1 | 10/2005 | Morley et al. |
| 2005/0261705 A1 | 11/2005 | Gist |
| 2006/0015133 A1 | 1/2006 | Grayzel |
| 2006/0058813 A1 | 3/2006 | Teague |
| 2006/0116693 A1 | 6/2006 | Weisenburgh |
| 2006/0135963 A1 | 6/2006 | Kick |
| 2006/0156875 A1 | 7/2006 | McRury et al. |
| 2006/0189891 A1 | 8/2006 | Waxman et al. |
| 2007/0016164 A1 | 1/2007 | Dudney et al. |
| 2007/0027443 A1 | 2/2007 | Rose |
| 2007/0027534 A1 | 2/2007 | Bergheim |
| 2007/0032906 A1 | 2/2007 | Sutherland et al. |
| 2007/0106304 A1 | 5/2007 | Hammack |
| 2007/0135803 A1 | 6/2007 | Belson |
| 2007/0208375 A1 | 9/2007 | Nishizawa |
| 2007/0213668 A1 | 9/2007 | Spitz |
| 2007/0239178 A1 | 10/2007 | Weitzner et al. |
| 2007/0250111 A1 | 10/2007 | Lu |
| 2007/0299427 A1 | 12/2007 | Yeung et al. |
| 2008/0015566 A1 | 1/2008 | Livneh |
| 2008/0021440 A1 | 1/2008 | Solomon |
| 2008/0033467 A1 | 2/2008 | Miyamoto et al. |
| 2008/0046122 A1 | 2/2008 | Manzo et al. |
| 2008/0065111 A1 | 3/2008 | Blumenkranz |
| 2008/0125698 A1 | 5/2008 | Greg et al. |
| 2008/0187101 A1 | 8/2008 | Gertner |
| 2008/0196533 A1 | 8/2008 | Bergamasco |
| 2008/0228104 A1 | 9/2008 | Uber et al. |
| 2009/0012507 A1 | 1/2009 | Culbertson et al. |
| 2009/0030446 A1 | 1/2009 | Measamer |
| 2009/0036900 A1 | 2/2009 | Moll |
| 2009/0043305 A1 | 2/2009 | Brodbeck |
| 2009/0082634 A1 | 3/2009 | Kathrani et al. |
| 2009/0088774 A1 | 4/2009 | Swarup et al. |
| 2009/0105723 A1 | 4/2009 | Dillinger |
| 2009/0131885 A1 | 5/2009 | Akahoshi |
| 2009/0161827 A1 | 6/2009 | Gertner et al. |
| 2009/0227998 A1 | 9/2009 | Aljuri |
| 2009/0248041 A1 | 10/2009 | Williams et al. |
| 2009/0248043 A1 | 10/2009 | Tierney et al. |
| 2009/0264878 A1 | 10/2009 | Carmel et al. |
| 2009/0270760 A1 | 10/2009 | Leimbach et al. |
| 2009/0287188 A1 | 11/2009 | Golden et al. |
| 2009/0299352 A1 | 12/2009 | Zerfas |
| 2009/0312773 A1 | 12/2009 | Cabrera et al. |
| 2010/0004642 A1 | 1/2010 | Lumpkin |
| 2010/0010504 A1 | 1/2010 | Simaan et al. |
| 2010/0011900 A1 | 1/2010 | Burbank |
| 2010/0011901 A1 | 1/2010 | Burbank |
| 2010/0016852 A1 | 1/2010 | Manzo et al. |
| 2010/0082017 A1 | 4/2010 | Zickler |
| 2010/0179632 A1 | 7/2010 | Bruszewski et al. |
| 2010/0204605 A1 | 8/2010 | Blakley |
| 2010/0204646 A1 | 8/2010 | Plicchi et al. |
| 2010/0217235 A1 | 8/2010 | Thorstenson |
| 2010/0225209 A1 | 9/2010 | Goldberg |
| 2010/0228249 A1 | 9/2010 | Mohr |
| 2010/0268211 A1 | 10/2010 | Manwaring et al. |
| 2010/0312141 A1 | 12/2010 | Keast et al. |
| 2010/0331858 A1 | 12/2010 | Simaan et al. |
| 2011/0015483 A1 | 1/2011 | Barbagli |
| 2011/0071541 A1 | 3/2011 | Prisco et al. |
| 2011/0071543 A1 | 3/2011 | Prisco et al. |
| 2011/0106146 A1 | 5/2011 | Jeong |
| 2011/0125165 A1 | 5/2011 | Simaan et al. |
| 2011/0152880 A1 | 6/2011 | Alvarez et al. |

(56) References Cited

U.S. PATENT DOCUMENTS

| | | |
|---|---|---|
| 2011/0160713 A1 | 6/2011 | Neuberger |
| 2011/0167611 A1 | 7/2011 | Williams |
| 2011/0213362 A1 | 9/2011 | Cunningham |
| 2011/0224660 A1 | 9/2011 | Neuberger et al. |
| 2011/0238064 A1 | 9/2011 | Williams et al. |
| 2011/0257641 A1 | 10/2011 | Hastings et al. |
| 2011/0276085 A1 | 11/2011 | Krzyzanowski |
| 2011/0313343 A1 | 12/2011 | Milutinovic et al. |
| 2012/0069167 A1 | 3/2012 | Liu et al. |
| 2012/0253277 A1 | 4/2012 | Tah et al. |
| 2012/0138586 A1 | 6/2012 | Webster et al. |
| 2012/0138660 A1 | 6/2012 | Shelton, IV et al. |
| 2012/0209315 A1 | 8/2012 | Amat |
| 2012/0232342 A1 | 9/2012 | Reydel |
| 2012/0253332 A1 | 10/2012 | Moll |
| 2012/0259320 A1 | 10/2012 | Loesel et al. |
| 2012/0296318 A1 | 11/2012 | Wellhofer et al. |
| 2013/0006144 A1 | 1/2013 | Clancy |
| 2013/0035537 A1 | 2/2013 | Wallace et al. |
| 2013/0053877 A1 | 2/2013 | BenMaamer |
| 2013/0066136 A1 | 3/2013 | Palese et al. |
| 2013/0085442 A1 | 4/2013 | Shtul et al. |
| 2013/0085486 A1 | 4/2013 | Boutoussov et al. |
| 2013/0096422 A1 | 4/2013 | Boctor |
| 2013/0096574 A1 | 4/2013 | Kang et al. |
| 2013/0110042 A1 | 5/2013 | Humphreys |
| 2013/0110107 A1 | 5/2013 | Smith et al. |
| 2013/0116716 A1 | 5/2013 | Bahls et al. |
| 2013/0144274 A1 | 6/2013 | Stefanchik et al. |
| 2013/0144395 A1 | 6/2013 | Stefanchik |
| 2013/0190796 A1 | 7/2013 | Tilson et al. |
| 2013/0225997 A1 | 8/2013 | Dillard et al. |
| 2013/0233908 A1 | 9/2013 | Knodel |
| 2013/0253267 A1 | 9/2013 | Collins |
| 2013/0303876 A1 | 11/2013 | Gelfand et al. |
| 2013/0310819 A1 | 11/2013 | Neuberger et al. |
| 2013/0334281 A1 | 12/2013 | Williams |
| 2013/0345686 A1 | 12/2013 | Brown |
| 2014/0005681 A1 | 1/2014 | Gee et al. |
| 2014/0039681 A1 | 2/2014 | Bowling |
| 2014/0046308 A1 | 2/2014 | Bischoff |
| 2014/0051985 A1 | 2/2014 | Fan et al. |
| 2014/0058365 A1 | 2/2014 | Bille |
| 2014/0058404 A1 | 2/2014 | Hammack |
| 2014/0058428 A1 | 2/2014 | Christopher |
| 2014/0100445 A1 | 4/2014 | Stenzel |
| 2014/0100558 A1* | 4/2014 | Schmitz ............... A61B 17/285 606/174 |
| 2014/0142591 A1 | 5/2014 | Alvarez et al. |
| 2014/0163318 A1 | 6/2014 | Swanstrom |
| 2014/0194859 A1 | 7/2014 | Ianchulev |
| 2014/0194905 A1 | 7/2014 | Kappel |
| 2014/0243849 A1 | 8/2014 | Saglam |
| 2014/0246473 A1 | 9/2014 | Auld |
| 2014/0275956 A1 | 9/2014 | Fan |
| 2014/0276723 A1 | 9/2014 | Parihar |
| 2014/0276956 A1 | 9/2014 | Crainich |
| 2014/0309655 A1 | 10/2014 | Gal et al. |
| 2014/0316203 A1 | 10/2014 | Carroux et al. |
| 2014/0357984 A1 | 12/2014 | Wallace et al. |
| 2014/0364870 A1 | 12/2014 | Alvarez et al. |
| 2015/0080879 A1 | 3/2015 | Trees |
| 2015/0119637 A1 | 4/2015 | Alvarez et al. |
| 2015/0127045 A1 | 5/2015 | Prestel |
| 2015/0133960 A1 | 5/2015 | Lohmeier |
| 2015/0164522 A1 | 6/2015 | Budiman |
| 2015/0201917 A1 | 7/2015 | Snow |
| 2015/0202085 A1 | 7/2015 | Lemonis |
| 2015/0250530 A1 | 9/2015 | Manzo et al. |
| 2015/0314110 A1 | 11/2015 | Park |
| 2016/0001038 A1 | 1/2016 | Romo et al. |
| 2016/0022289 A1 | 1/2016 | Wan |
| 2016/0022466 A1 | 1/2016 | Pedtke |
| 2016/0030073 A1 | 2/2016 | Lsakov |
| 2016/0045208 A1 | 2/2016 | Ciulla |
| 2016/0051318 A1 | 2/2016 | Manzo et al. |
| 2016/0066935 A1 | 3/2016 | Nguyen et al. |
| 2016/0158490 A1 | 6/2016 | Leeflang |
| 2016/0183841 A1 | 6/2016 | Duindam et al. |
| 2016/0199984 A1 | 7/2016 | Lohmeier et al. |
| 2016/0235495 A1 | 8/2016 | Wallace et al. |
| 2016/0249932 A1 | 9/2016 | Rogers et al. |
| 2016/0270865 A1 | 9/2016 | Landey et al. |
| 2016/0287279 A1 | 10/2016 | Bovay et al. |
| 2016/0303743 A1 | 10/2016 | Rockrohr |
| 2016/0310146 A1 | 10/2016 | Levy et al. |
| 2016/0331358 A1 | 11/2016 | Gordon |
| 2016/0367324 A1 | 12/2016 | Sato et al. |
| 2017/0007337 A1 | 1/2017 | Dan |
| 2017/0049471 A1 | 2/2017 | Gaffney et al. |
| 2017/0055995 A1 | 3/2017 | Weier |
| 2017/0065227 A1 | 3/2017 | Marrs |
| 2017/0095234 A1 | 4/2017 | Prisco et al. |
| 2017/0095295 A1 | 4/2017 | Overmyer |
| 2017/0119481 A1 | 5/2017 | Romo et al. |
| 2017/0135706 A1 | 5/2017 | Frev |
| 2017/0151416 A1 | 6/2017 | Kutikov |
| 2017/0165011 A1 | 6/2017 | Bovay et al. |
| 2017/0172553 A1 | 6/2017 | Chaplin |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0252096 A1 | 9/2017 | Felder |
| 2017/0265923 A1 | 9/2017 | Privitera |
| 2017/0265954 A1 | 9/2017 | Burbank |
| 2017/0290631 A1 | 10/2017 | Lee et al. |
| 2017/0319289 A1 | 11/2017 | Neff et al. |
| 2017/0333679 A1 | 11/2017 | Jiang |
| 2017/0340396 A1 | 11/2017 | Romo et al. |
| 2017/0367782 A1 | 12/2017 | Schuh et al. |
| 2018/0000563 A1 | 1/2018 | Shanjani et al. |
| 2018/0025666 A1 | 1/2018 | Ho et al. |
| 2018/0049824 A1 | 2/2018 | Harris |
| 2018/0177556 A1 | 6/2018 | Noonan et al. |
| 2018/0193049 A1 | 7/2018 | Heck et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0296285 A1 | 10/2018 | Simi et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0083183 A1 | 3/2019 | Moll et al. |
| 2019/0099231 A1 | 4/2019 | Bruehwiler |
| 2019/0105776 A1 | 4/2019 | Ho et al. |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0228528 A1 | 7/2019 | Mintz et al. |
| 2019/0239890 A1 | 8/2019 | Stokes |
| 2019/0246882 A1 | 8/2019 | Graetzel et al. |
| 2019/0262086 A1 | 8/2019 | Connolly et al. |
| 2019/0269468 A1 | 9/2019 | Hsu et al. |

(56) References Cited

U.S. PATENT DOCUMENTS

| | | |
|---|---|---|
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan |
| 2019/0298460 A1 | 10/2019 | Al-Jadda |
| 2019/0298465 A1 | 10/2019 | Chin |
| 2019/0314616 A1 | 10/2019 | Moll et al. |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0022767 A1 | 1/2020 | Hill |
| 2020/0039086 A1 | 2/2020 | Meyer |
| 2020/0046434 A1 | 2/2020 | Graetzel |
| 2020/0054408 A1 | 2/2020 | Schuh et al. |
| 2020/0060516 A1 | 2/2020 | Baez |
| 2020/0093549 A1 | 3/2020 | Chin |
| 2020/0093554 A1 | 3/2020 | Schuh |
| 2020/0100845 A1 | 4/2020 | Julian |
| 2020/0100855 A1 | 4/2020 | Leparmentier |
| 2020/0101264 A1 | 4/2020 | Jiang |
| 2020/0121502 A1 | 4/2020 | Kintz |
| 2020/0146769 A1 | 5/2020 | Eyre |
| 2020/0163726 A1 | 5/2020 | Tanner |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |

FOREIGN PATENT DOCUMENTS

| | | |
|---|---|---|
| CN | 103298414 | 9/2013 |
| CN | 205729413 | 11/2016 |
| EP | 1 321 106 | 6/2003 |
| EP | 1 849 423 | 10/2007 |
| EP | 2 341 847 | 10/2013 |
| EP | 3 181 069 | 6/2017 |
| EP | 2 675 383 | 7/2017 |
| JP | 2005-270464 | 10/2005 |
| WO | WO 11/161218 | 12/2011 |
| WO | WO 13/107468 | 7/2013 |
| WO | WO 13/130895 | 9/2013 |
| WO | WO 17/114855 | 7/2017 |
| WO | WO 18/069679 | 4/2018 |
| WO | WO 18/189722 | 10/2018 |

* cited by examiner

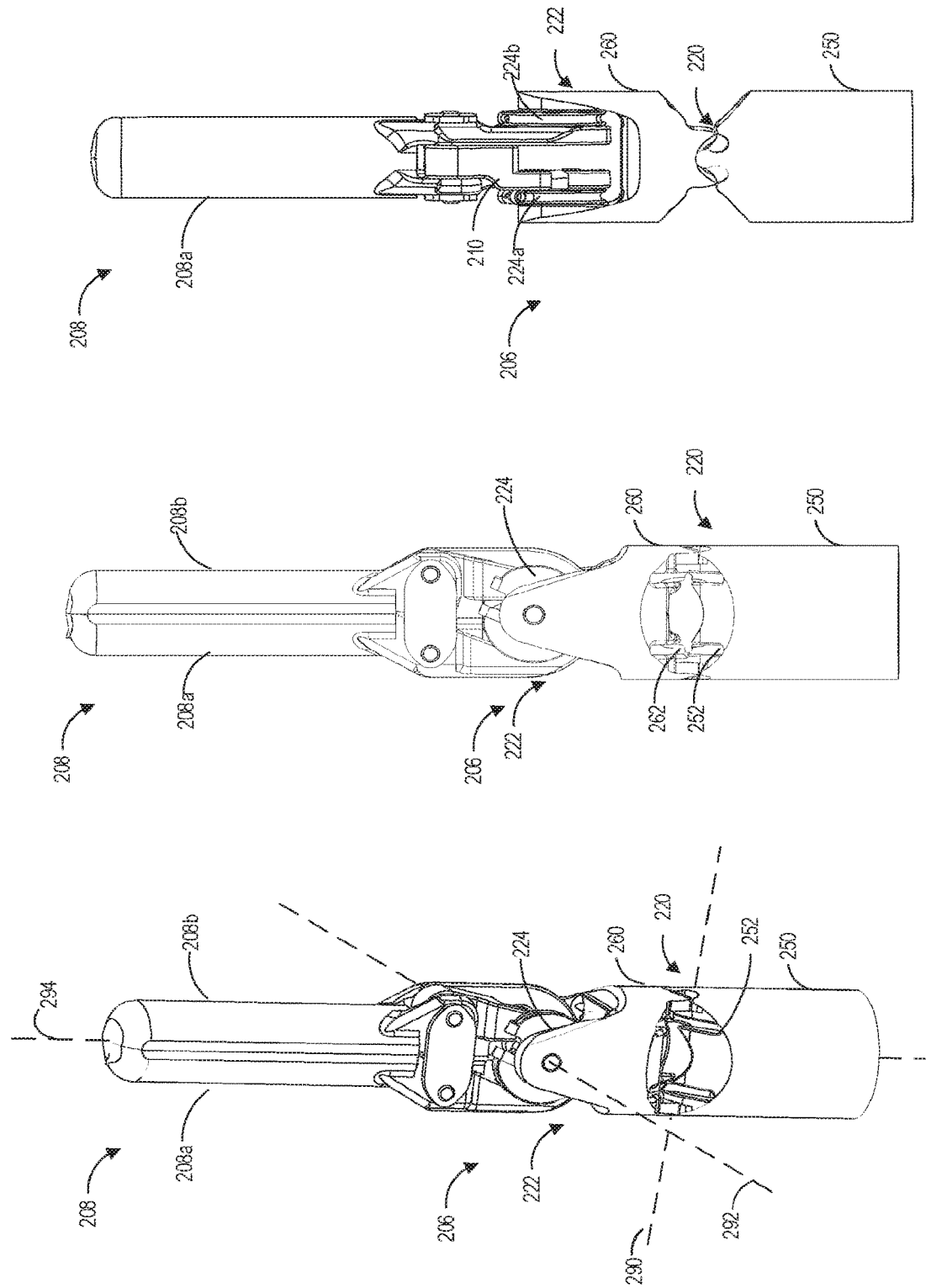

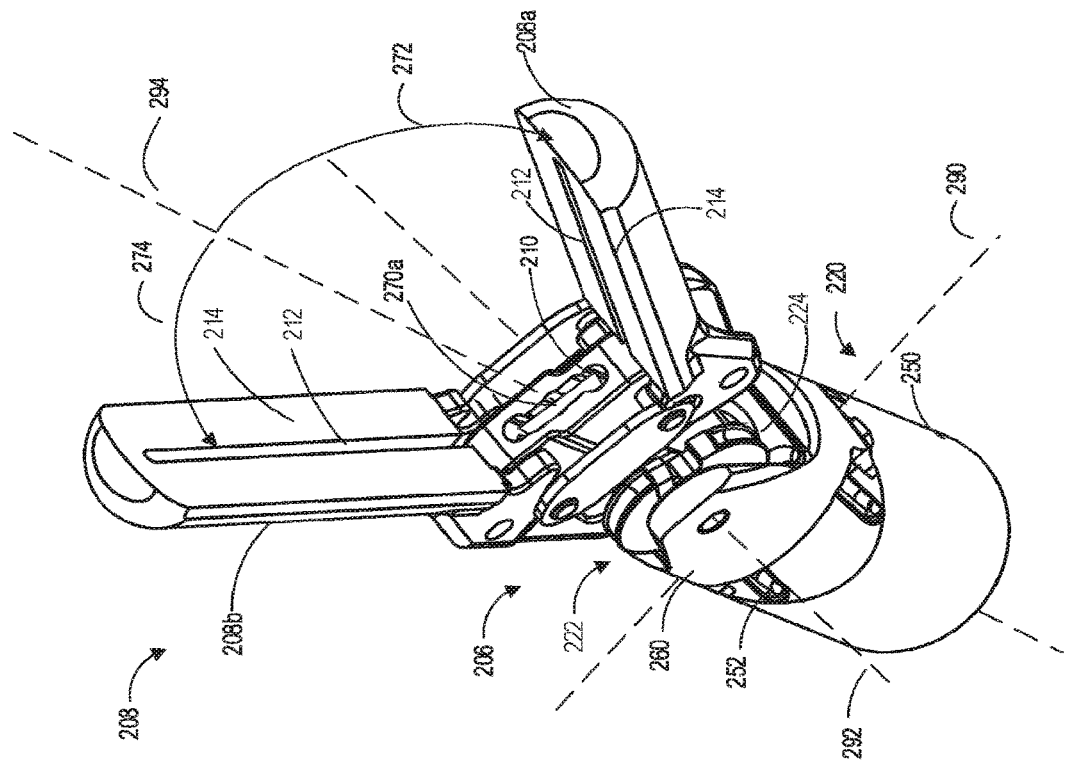
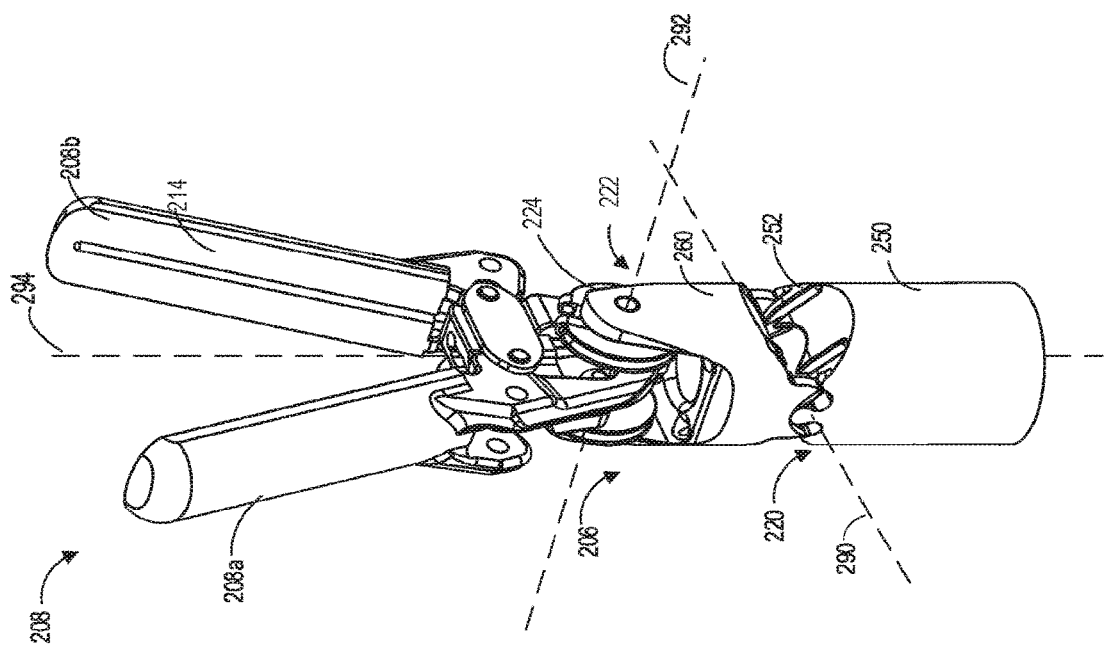
FIG. 23B
FIG. 23A

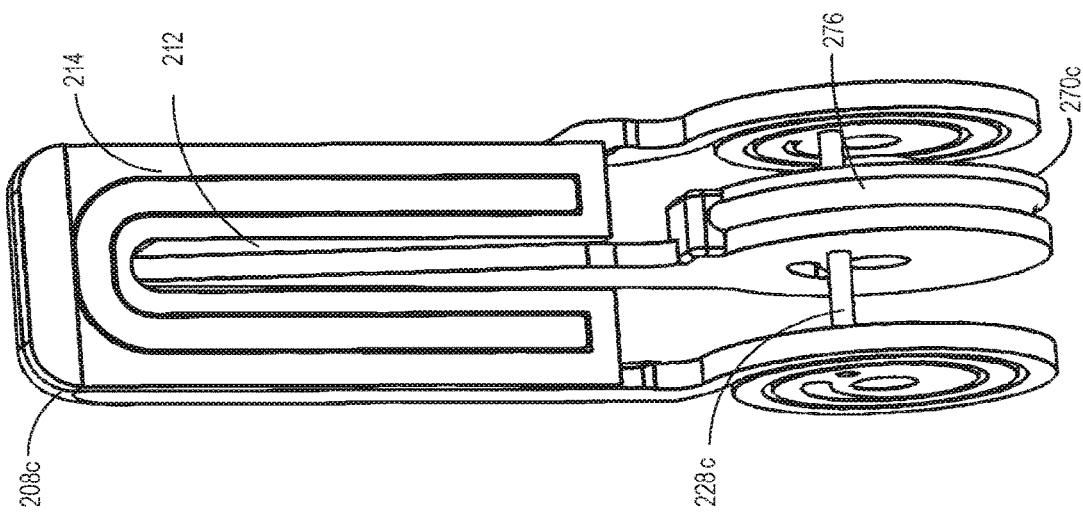
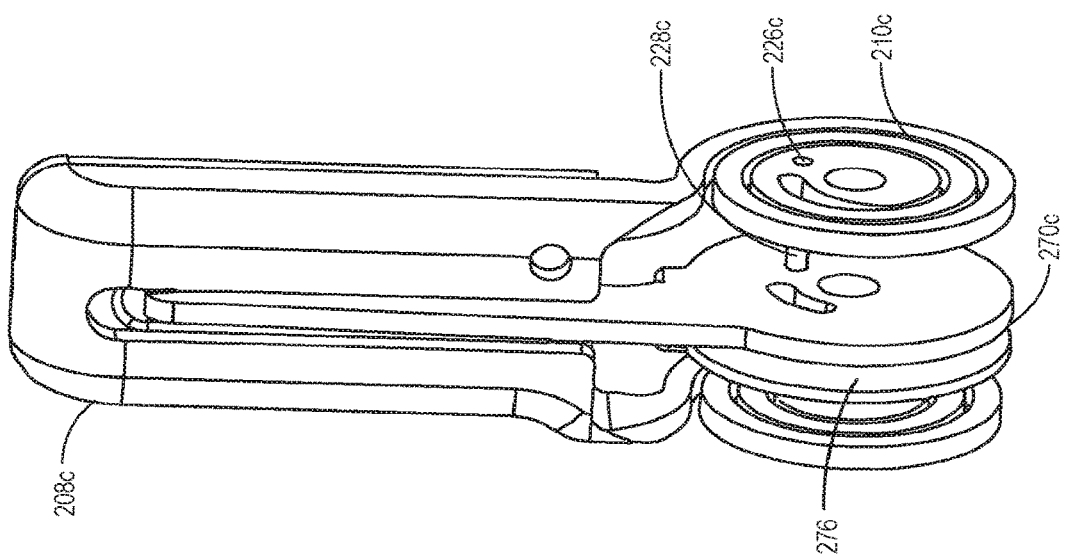

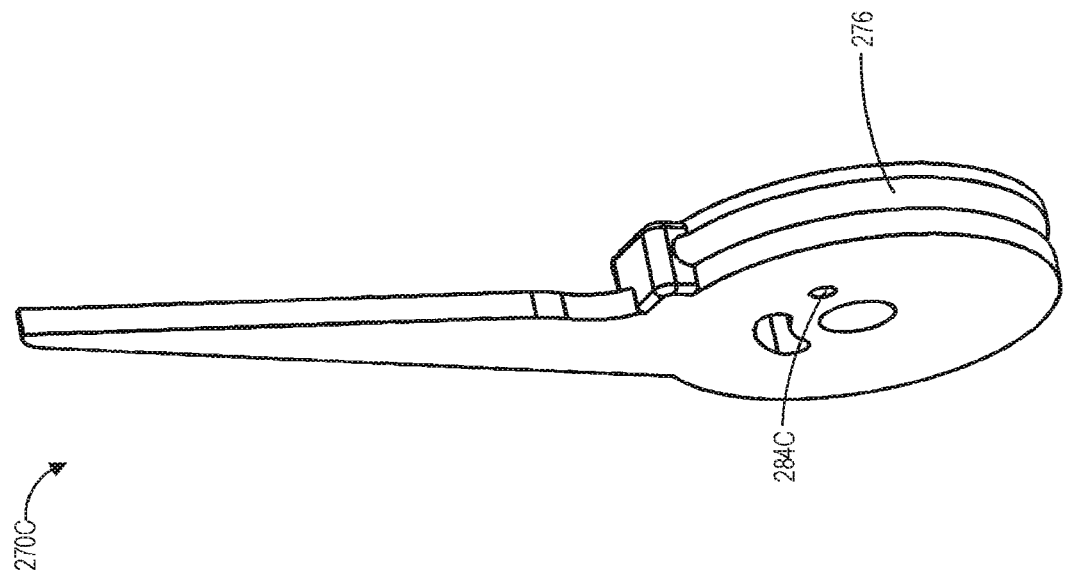

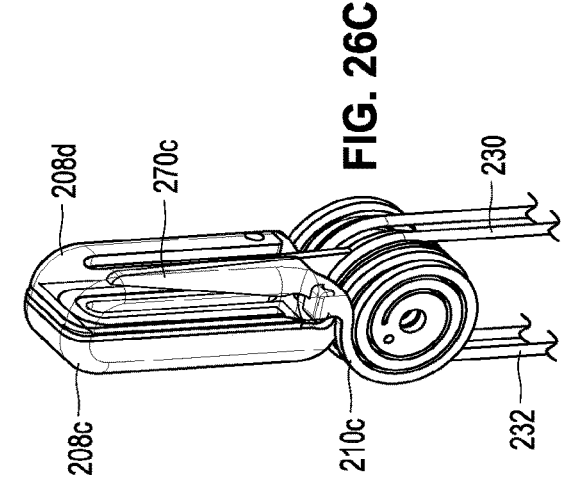
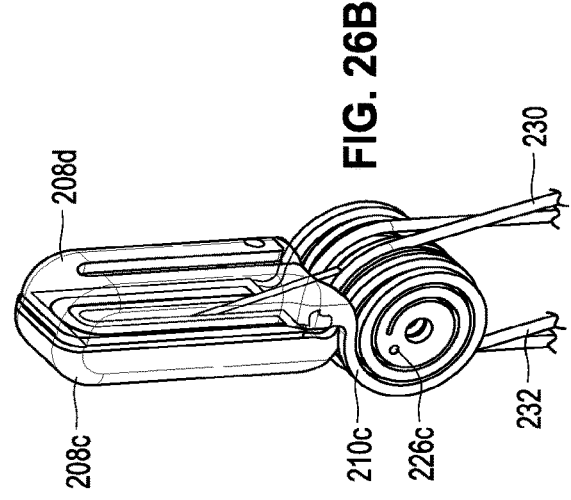
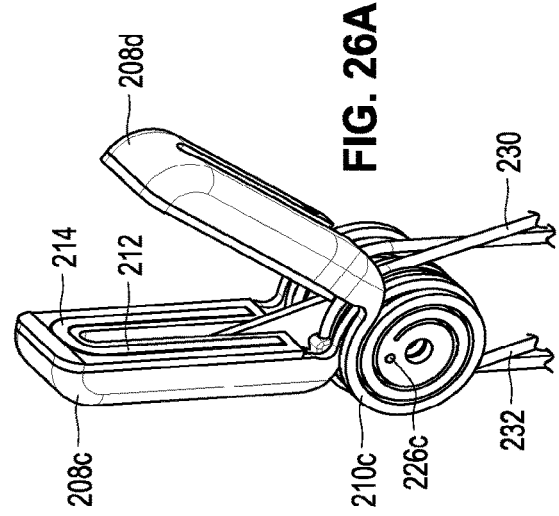
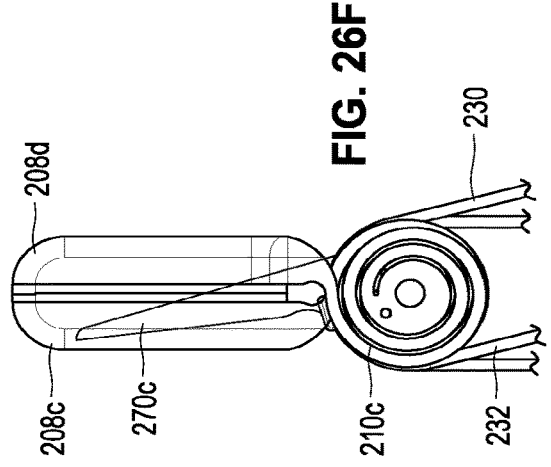
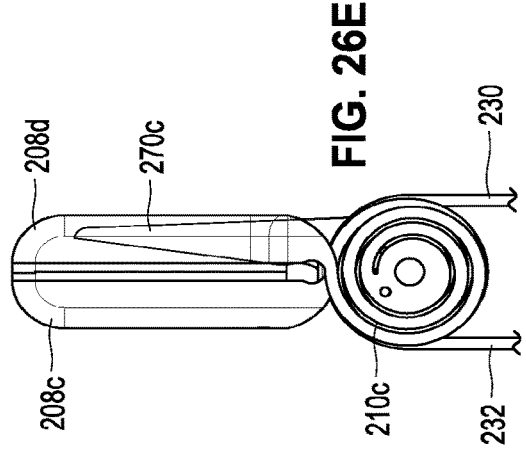
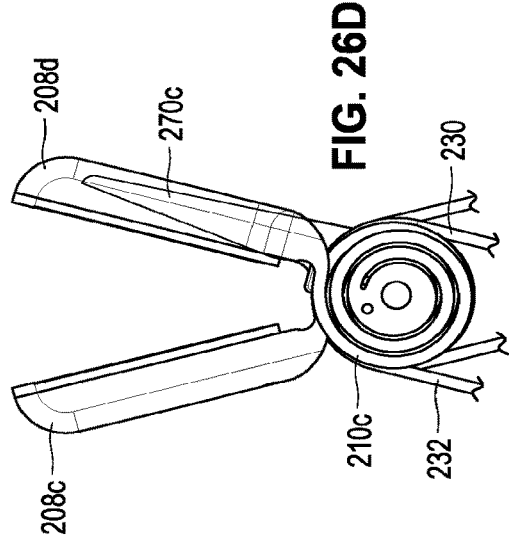

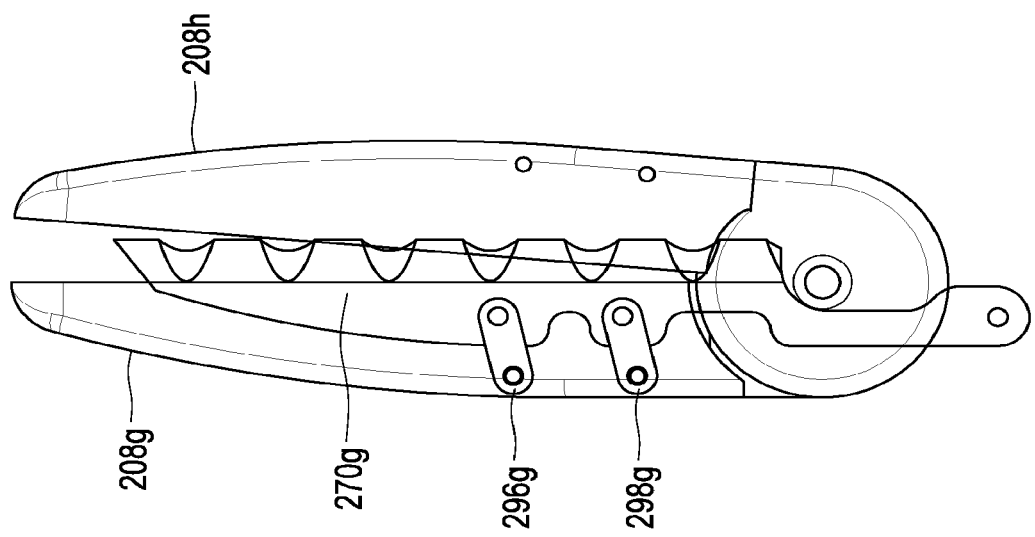
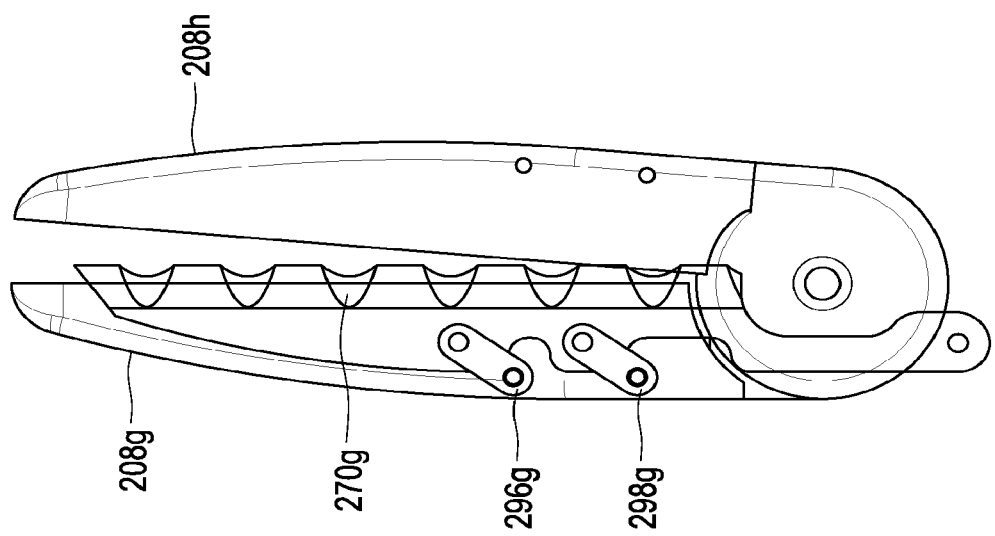
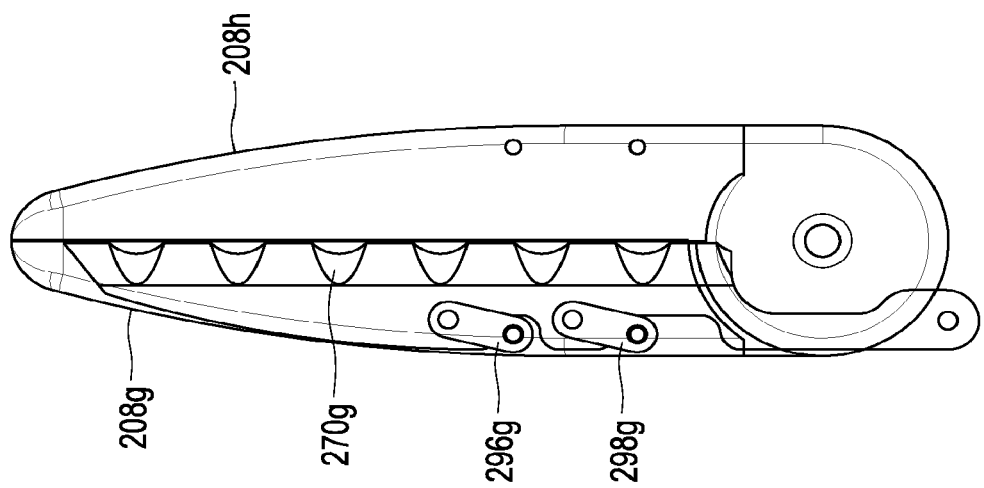
FIG. 28C
FIG. 28B
FIG. 28A

SYSTEMS AND INSTRUMENTS FOR TISSUE SEALING

CROSS-REFERENCE TO RELATED APPLICATION(S)

This application is a divisional application of U.S. application Ser. No. 16/563,480, filed Sep. 6, 2019, which claims the benefit of U.S. Provisional Application No. 62/742,855, filed Oct. 8, 2018, each of which is hereby incorporated by reference in its entirety.

TECHNICAL FIELD

The systems and methods disclosed herein are directed to medical instrument and in particular, to a medical instrument for a robotic medical system.

BACKGROUND

Medical procedures, such as laparoscopy, may involve accessing and visualizing an internal region of a patient. In a laparoscopic procedure, a medical instrument can be inserted into the internal region through a laparoscopic access port.

In certain procedures, a robotically enabled medical system may be used to control the insertion and/or manipulation of the medical instrument and end effector. The robotically enabled medical system may include a robotic arm or any other instrument positioning device. The robotically enabled medical system may also include a controller used to control the positioning of the instrument during the procedure.

SUMMARY

In a first aspect, a multi-functional surgical instrument comprises an elongate shaft extending between a proximal end and a distal end, a wrist extending from the distal end of the elongate shaft, an end effector extending from the wrist, and at least one rotary cutter extending from the wrist and positioned at least partially within a recess formed in a face of the first jaw. The end effector comprises a first jaw and a second jaw, the first and second jaw being moveable between an open position in which ends of the jaws are separated from each other and a closed position in which the ends of the jaws are closer to each other as compared to the open position.

The surgical instrument may further include one or more of the following features in any combination: (a) wherein the face of the first jaw engages tissue; (b) wherein the instrument further comprises a conducting material positioned on the face of the first jaw; (c) wherein the at least one rotary cutter is moveable between a first position in which a cutting edge of the rotary cutter is recessed from the first jaw and a second position in which the cutting edge of the rotary cutter extends beyond the face of the first jaw and against or past the face of the second jaw; (d) wherein the at least one rotary cutter is moveable between a first position in which a cutting edge of the rotary cutter is positioned within the recess formed in the first jaw and a second position in which the cutting edge of the rotary cutter extends closer to a midline of the instrument than in the first position; (e) wherein the at least one rotary cutter is offset from the edge of the first jaw, such that the rotary cutter can remain in the first position when the first and second jaw are in the closed position; (f) wherein the rotary cutter is coupled to the first jaw; (h) wherein the motion of the rotary cutter is coupled to the first jaw by a spring; (i) wherein at least one of the rotary cutter and the first jaw comprises a spring; (j) wherein rotation of the rotary cutter about a first axis causes the first jaw to rotate about the first axis until the face of the first jaw contacts a face of the second jaw, and wherein upon the face of the first jaw contacting the face of the second jaw further rotation of the rotary cutter causes the rotary cutter to move from the first position to the second position; (k) wherein the spring is a torsion spring; (l) wherein the at least one rotary cutter and the first jaw are actuated by a single actuation mechanism; (m) wherein the single actuation mechanism comprises one or more tension cables; (n) wherein the single actuation mechanism moves the first and second jaws between the open position and closed position; and wherein the single actuation mechanism moves the at least one rotary cutter between the first position and the second position; (o) wherein the single actuation mechanism is first actuated to move the first and second jaws from the open position to the closed position; and wherein the single actuation mechanism is further actuated to move the at least one rotary cutter from the first position to the second position; (p) wherein the at least one rotary cutter comprises a second rotary cutter positioned in a recess formed in the second jaw; (q) wherein the first and second rotary cutters comprise a dual-blade scissor; (r) wherein the first and second rotary cutters are moveable between a first position in which ends of the first and second rotary cutters are separated from each other and a second position in which the ends of the first and second rotary cutters are closer to each other as compared to the first position; (s) wherein the first rotary cutter is offset from the face of the first jaw and the second rotary cutter is offset from the face of the second jaw, such that the first and second rotary cutters remain in the first position when the first and second jaw are in the closed position; (t) wherein the rotary cutter is coupled to the first jaw by a first spring; and wherein the second rotary cutter is coupled to the second jaw by a second spring; (u) wherein the first rotary cutter and the first jaw are actuated by a first actuation mechanism, and wherein the second rotary cutter and the second jaw are actuated by a second actuation mechanism; (v) wherein the first and second actuation mechanism each comprises one or more tension cables (w) wherein the first actuation mechanism moves the first jaw between the open position and the closed position; wherein the first actuation mechanism moves the first rotary cutter between the first position and the second position; wherein the second actuation mechanism moves the second jaw between the open position and the closed position; and wherein the second actuation mechanism moves the second rotary cutter between the first position and the second position; (x) wherein the first actuation mechanism is first actuated to move the first jaw from the open position to the closed position; wherein the second actuation mechanism is first actuated to move the second jaw from the open position to the closed position; wherein the first actuation mechanism is further actuated to move the first rotary cutter from the first position to the second position; and wherein the second actuation mechanism is further actuated to move the second rotary cutter from the first position to the second position; (y) wherein the at least one rotary cutter comprises an arced scythe; (z) wherein the at least one rotary cutter comprises a serrated blade; (aa) wherein the at least one rotary cutter comprises a blade and an anvil; (bb) wherein the at least one rotary cutter comprises a four-bar linkage with at least one pin in a slot; and/or (cc) wherein the at least one rotary cutter comprises a four-bar linkage with a cable or belt constraint.

In another aspect, a surgical instrument comprises an elongate shaft extending between a proximal end and a distal end, a wrist extending from the distal end of the elongate shaft, an end effector extending from the wrist, a cutter positioned within a recess formed in the first jaw and/or the second jaw; and a pivot bar coupling the cutter to the first jaw. The end effector comprises a first jaw and a second jaw, the first and second jaw being moveable between an open position in which ends of the jaws are separated from each other and a closed position in which the ends of the jaws are closer to each other as compared to the open position. The pivot bar may be pivotable about an axis to move the cutter from a first position in which a cutting edge of the cutter is positioned within the recess of the first jaw and a second position in which the cutting edge of the cutter extends beyond the recess of the first jaw.

The surgical instrument may further include one or more of the following features in any combination: (a) wherein the instrument includes a second pivot bar coupled to the cutter and pivotable about a second axis; (b) wherein the first jaw, the cutter and the first and second pivot bars form a four-bar linkage; (d) wherein the four-bar linkage is in the form of a parallelogram; and/or (e) wherein the four-bar linkage has a first side and an opposing second side, wherein the first side is not equal to the second side.

In another aspect, a method of using a multi-functional medical instrument, the method comprises (i) providing a multi-functional instrument having a first jaw and a second jaw, (ii) changing a relative position of the first jaw and second jaw from an open position to a closed position, wherein ends of the first jaw and the second jaw are positioned closer to one another in the closed position than in the open position, wherein in the closed position the first jaw and the second jaw can grip tissue within a patient; and (iii) deploying at least one cutter in a rotary motion to cut tissue within the patient.

The method may further include one or more of the following features in any combination: (a) wherein changing the relative position of the first jaw and the second jaw comprises moving the first jaw closer to a midline of the instrument; (b) wherein a single actuation mechanism moves the first jaw and deploys the at least one cutter; (c) wherein changing the relative position of the first jaw and the second jaw comprises moving only one of the first jaw and the second jaw relative to the other; (d) wherein changing the relative position of the first jaw and the second jaw comprising moving both the first jaw and the second jaw; and € wherein the at least one cutter comprises a first blade and a second blade.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 22A illustrates a perspective view of a first embodiment of a surgical effector.

FIG. 22B illustrates a side view of the first embodiment of the surgical effector shown in FIG. 22A.

FIG. 22C illustrates a front view of the first embodiment of the surgical effector shown in FIGS. 22A-22B.

FIG. 23A illustrates a perspective side view of the first embodiment of a surgical effector of FIGS. 22A-C in a different position.

FIG. 23B illustrates a perspective top view of the first embodiment of the surgical effector shown in FIG. 23A.

FIG. 24C illustrates a perspective rear view of the jaw half of the second embodiment of the surgical effector shown in FIGS. 24A-24B.

FIG. 24D illustrates a perspective front view of the jaw half of the second embodiment of the surgical effector shown in FIGS. 24A-24C.

FIG. 25 illustrates a perspective side view of the rotary cutter of the second embodiment of the surgical effector shown in FIGS. 24A-D.

FIG. 26A illustrates a perspective view of the second embodiment of the surgical effector shown in FIG. 24A-D in an open position.

FIG. 26B illustrates a perspective view of the second embodiment of the surgical effector shown in FIG. 26A in a closed position with cutters not actuated.

FIG. 26C illustrates a perspective view of the second embodiment of the surgical effector shown in FIG. 26A in a closed position with cutters actuated.

FIG. 26D illustrates a front view of the second embodiment of the surgical effector corresponding to the open position in FIG. 26A.

FIG. 26E illustrates a front view of the second embodiment of the surgical effector corresponding to the closed position with cutters not actuated in FIG. 26B.

FIG. 26F illustrates a front view of the second embodiment of the surgical effector corresponding to the closed position with cutters actuated in FIG. 26C.

FIG. 28A illustrates a front view of a fourth embodiment of a surgical effector.

FIG. 28B illustrates a front view of the fourth embodiment of the surgical effector shown in FIG. 28A in a different position.

FIG. 28C illustrates a front view of the fourth embodiment of the surgical effector shown in FIGS. 28A-28B in a different position.

DETAILED DESCRIPTION

1. Overview.

Aspects of the present disclosure may be integrated into a robotically enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
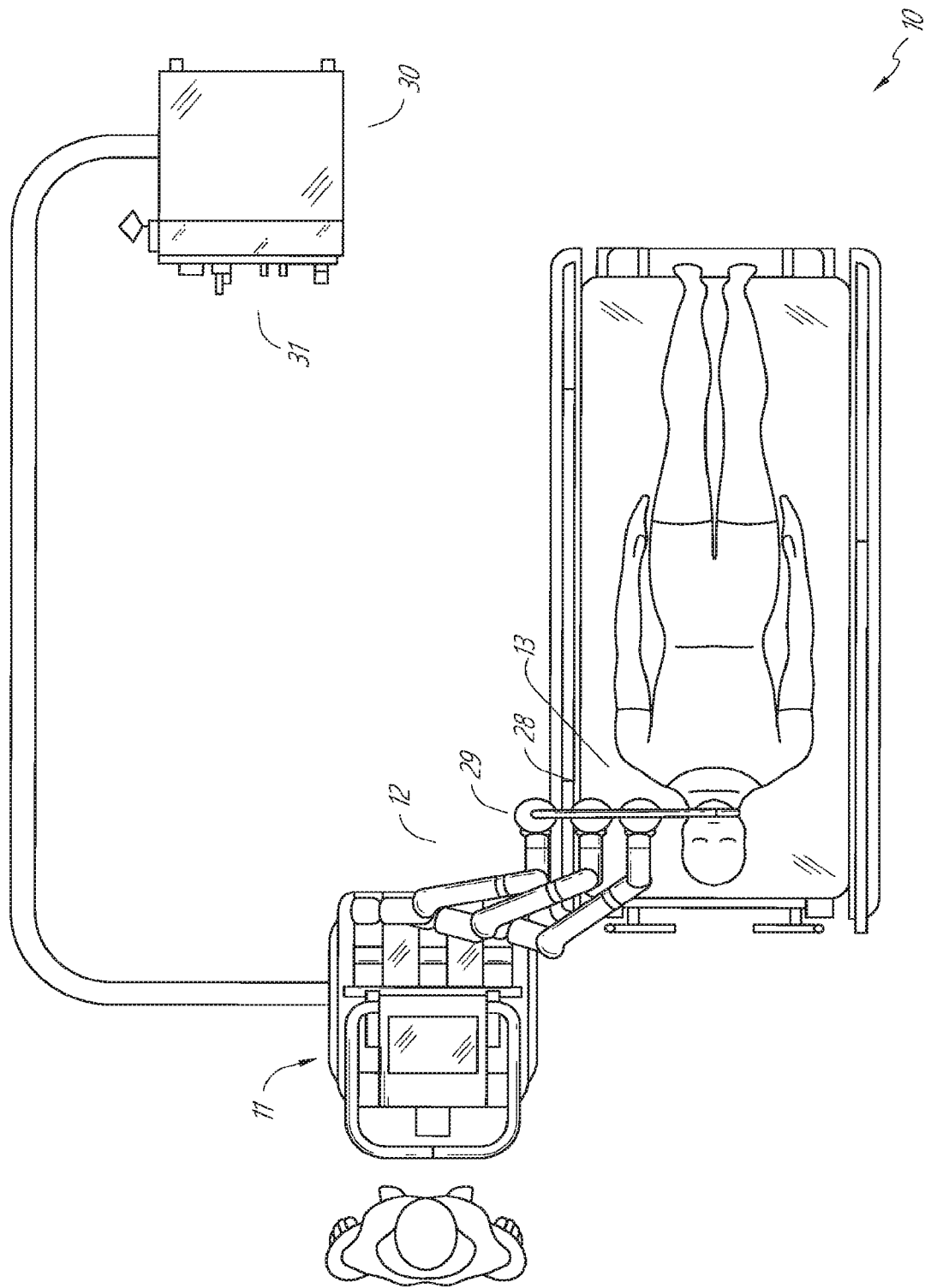
FIG. 1 illustrates an embodiment of a cart-based robotic system arranged for diagnostic and/or therapeutic bronchoscopy procedure(s).
Figure 2:
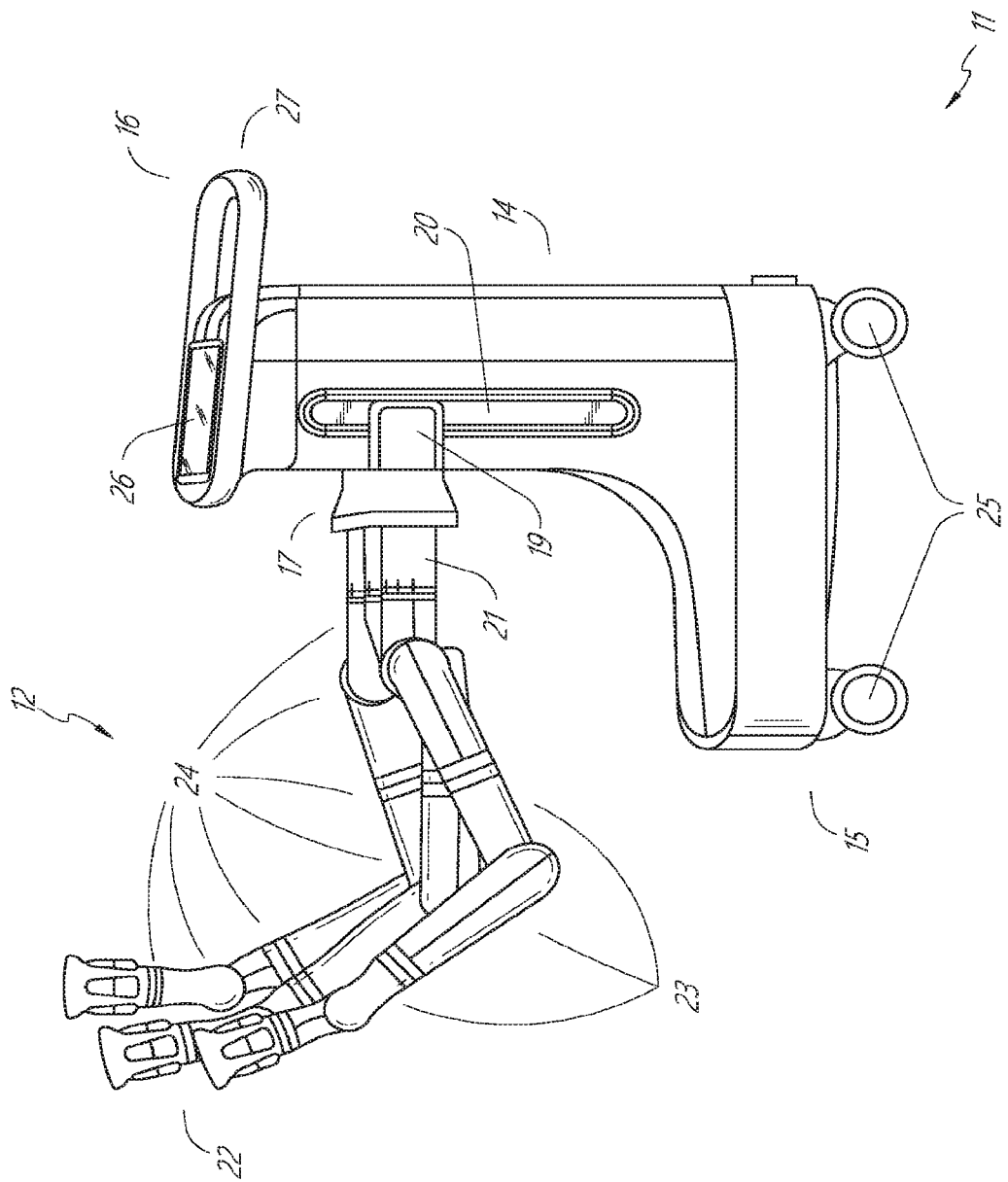
FIG. 2 depicts further aspects of the robotic system of FIG. 1.

The robotically enabled medical system may be configured in a variety of ways depending on the particular procedure. FIG. 1 illustrates an embodiment of a cart-based robotically enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
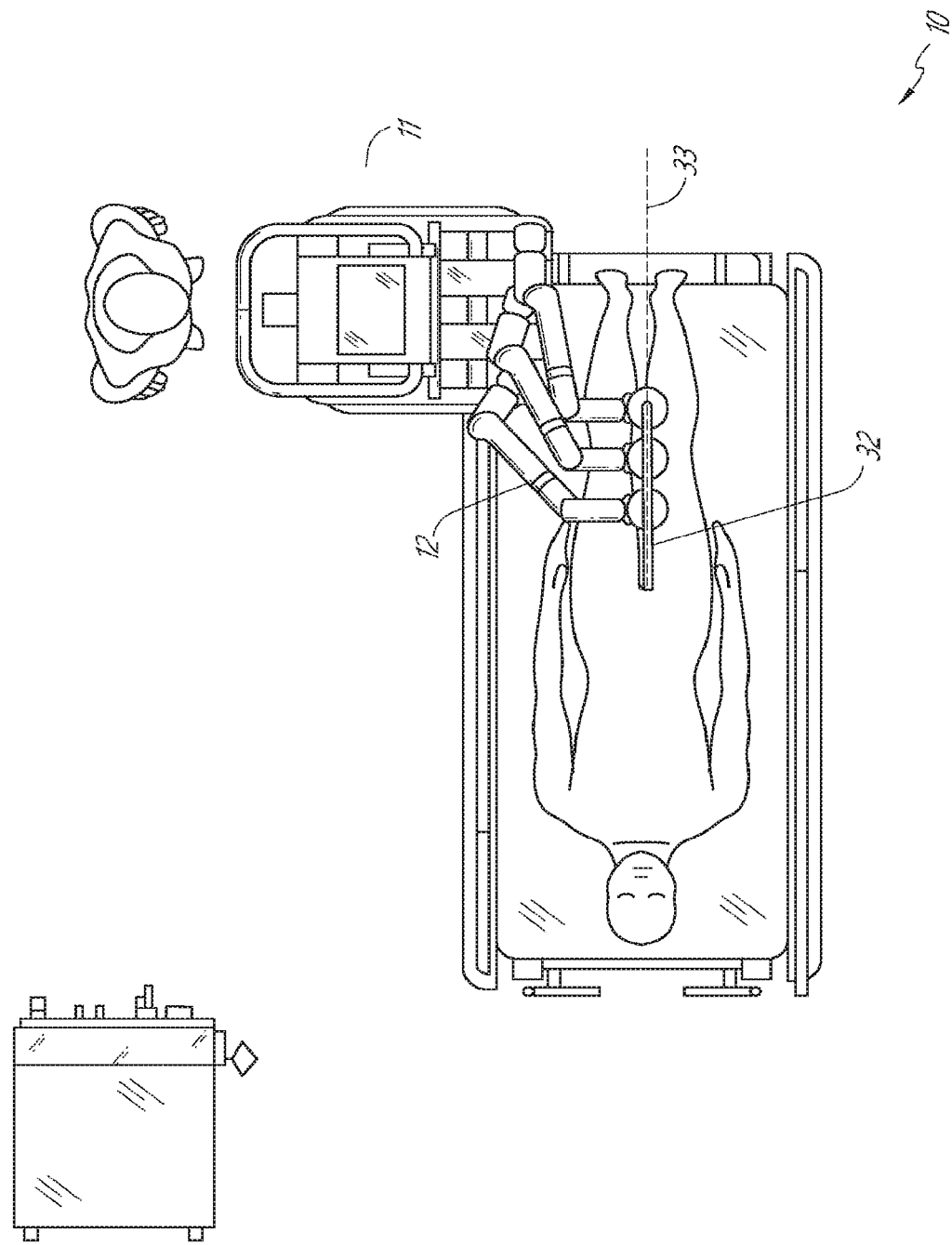
FIG. 3 illustrates an embodiment of the robotic system of FIG. 1 arranged for ureteroscopy.

FIG. 3 illustrates an embodiment of a robotically enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
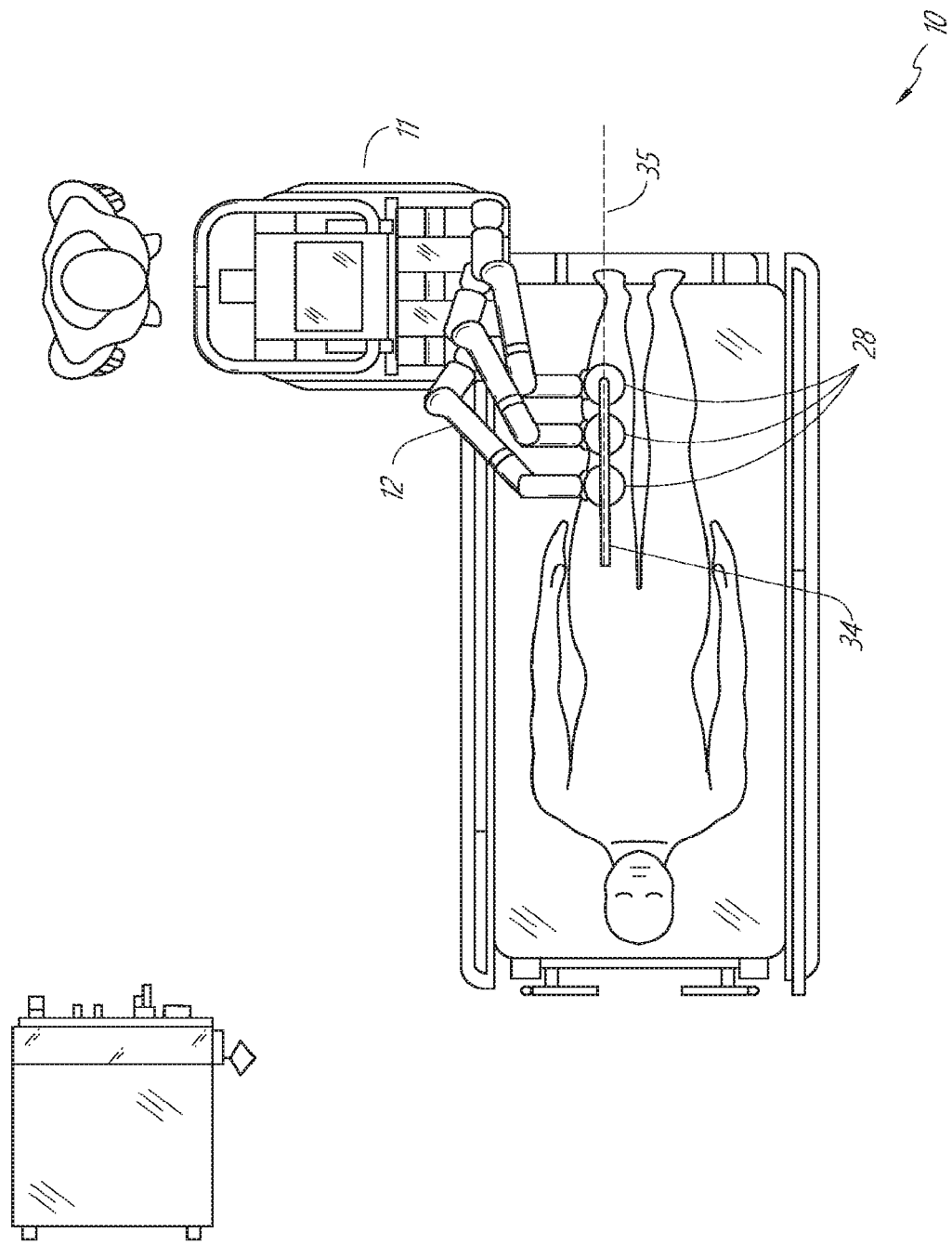
FIG. 4 illustrates an embodiment of the robotic system of FIG. 1 arranged for a vascular procedure.

FIG. 4 illustrates an embodiment of a robotically enabled system similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

Robotic System—Table.

Figure 5:
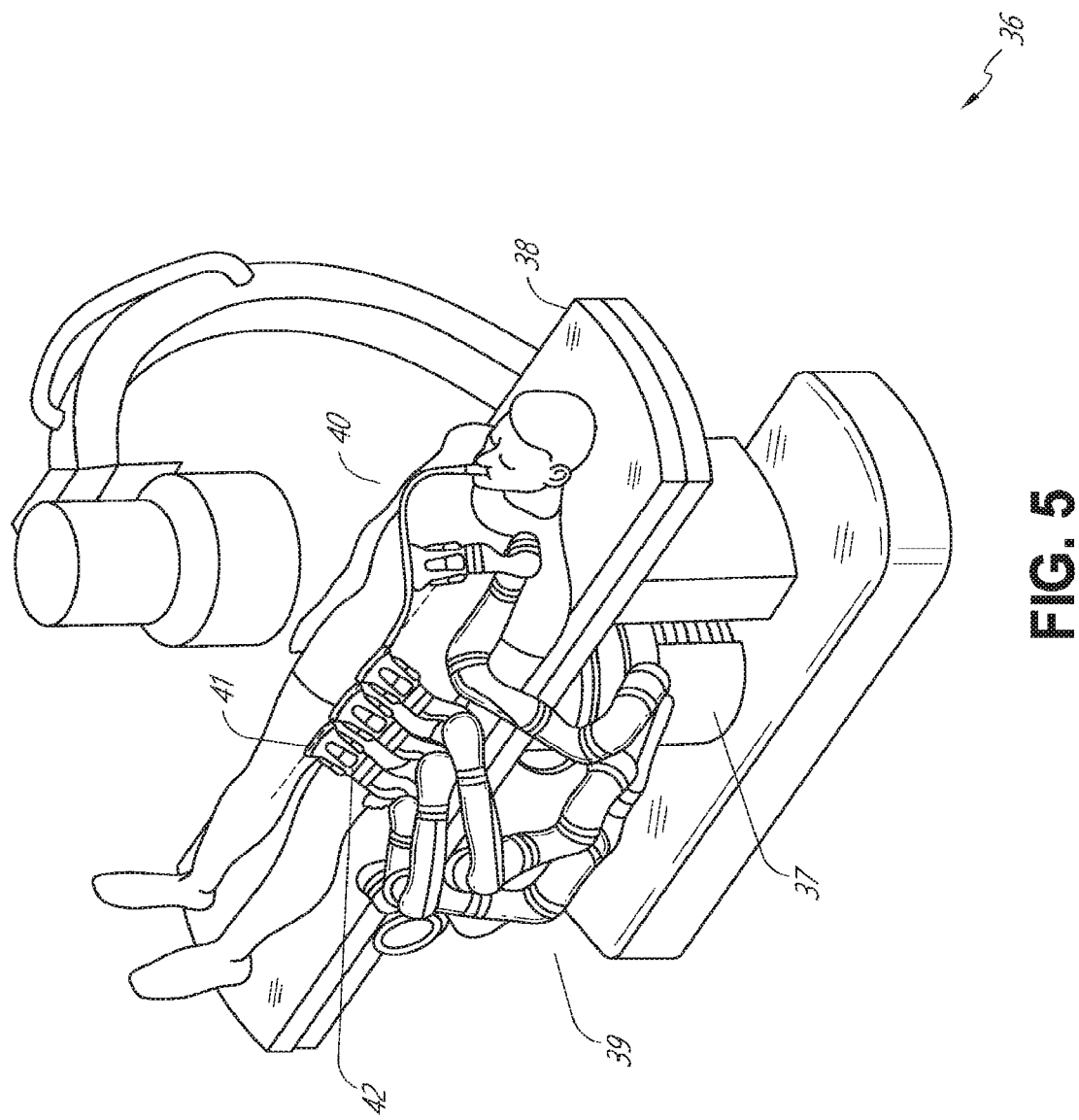
FIG. 5 illustrates an embodiment of a table-based robotic system arranged for a bronchoscopy procedure.

Embodiments of the robotically enabled medical system may also incorporate the patient's table. Incorporation of the table reduces the amount of capital equipment within the operating room by removing the cart, which allows greater access to the patient. FIG. 5 illustrates an embodiment of such a robotically enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
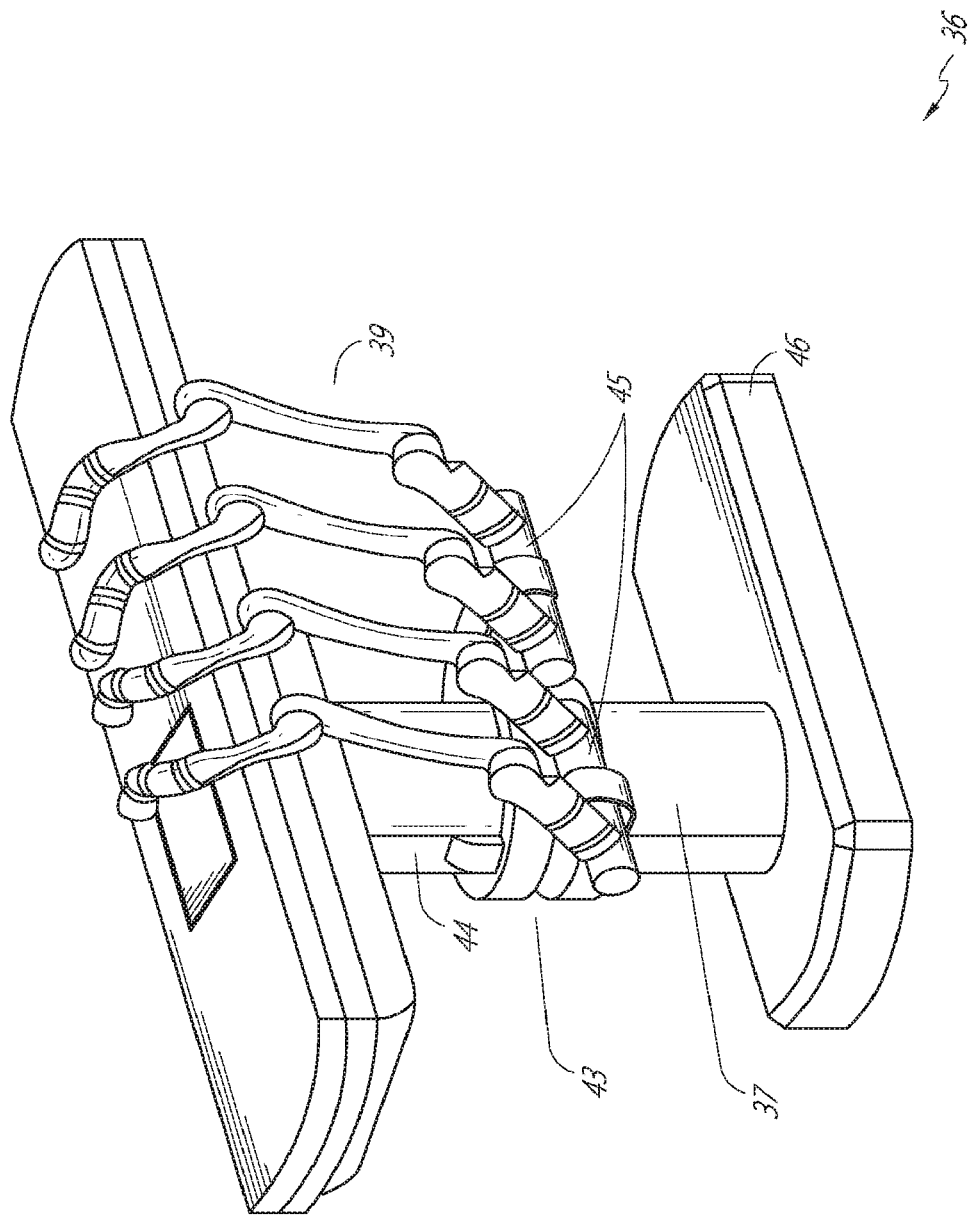
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
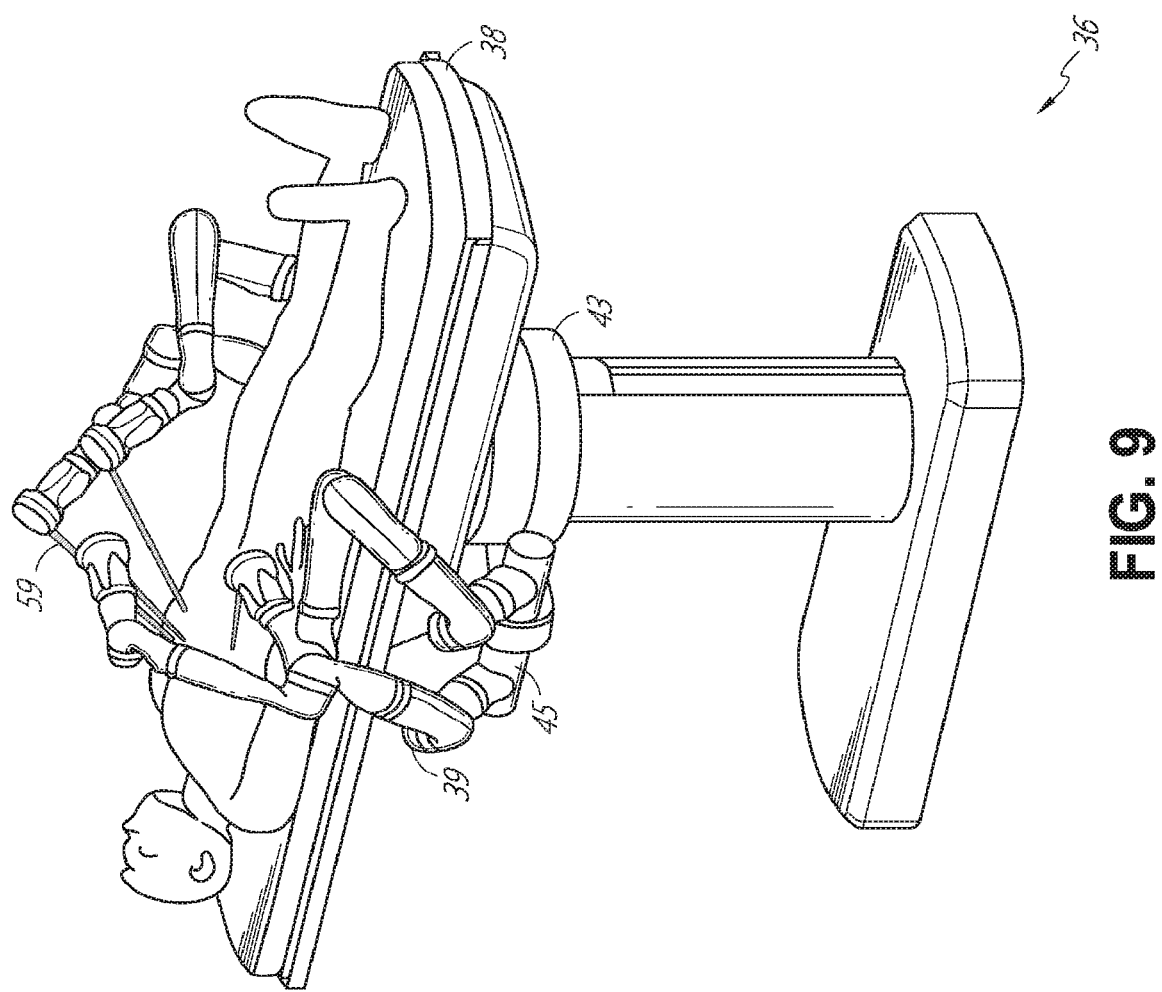
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
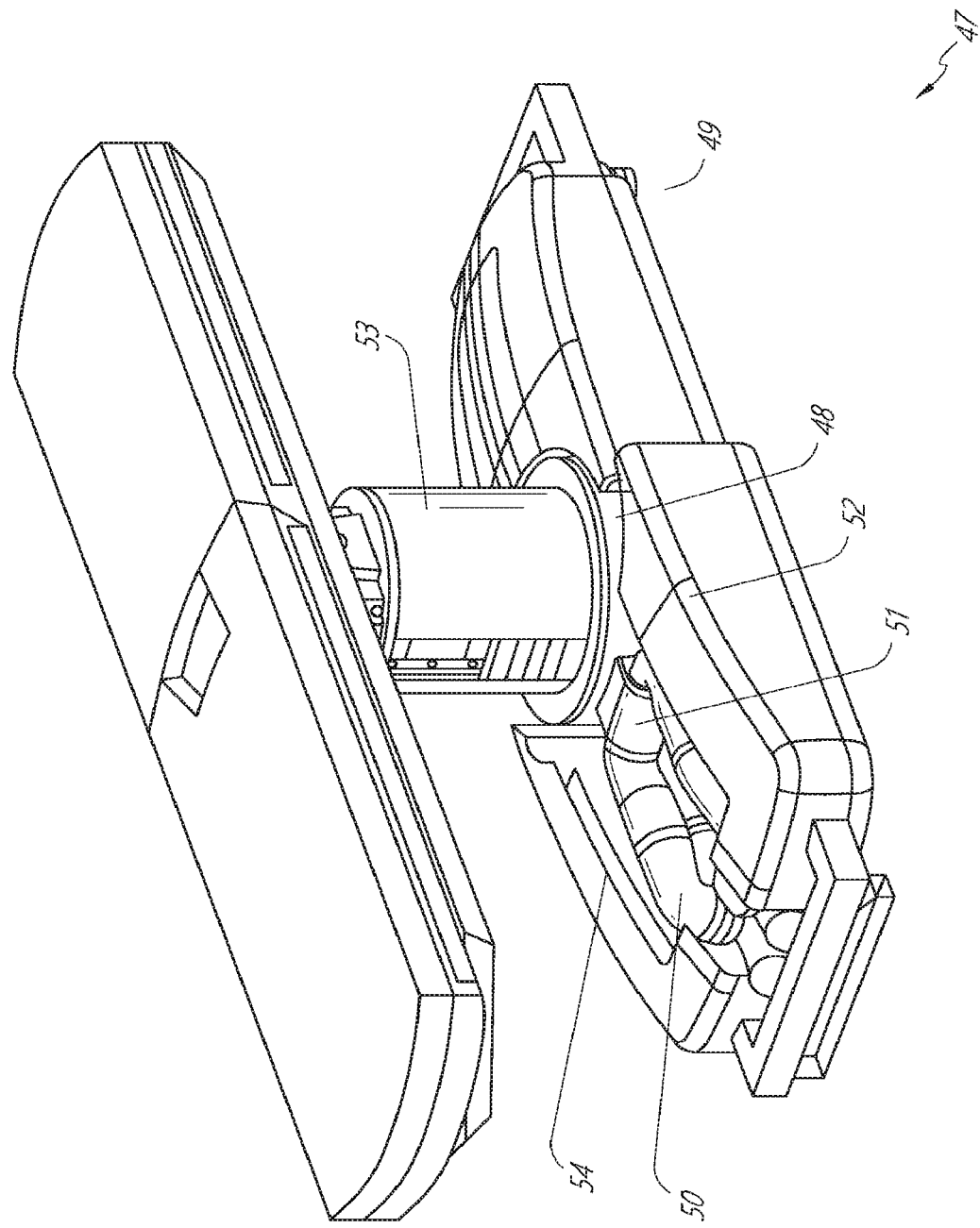
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
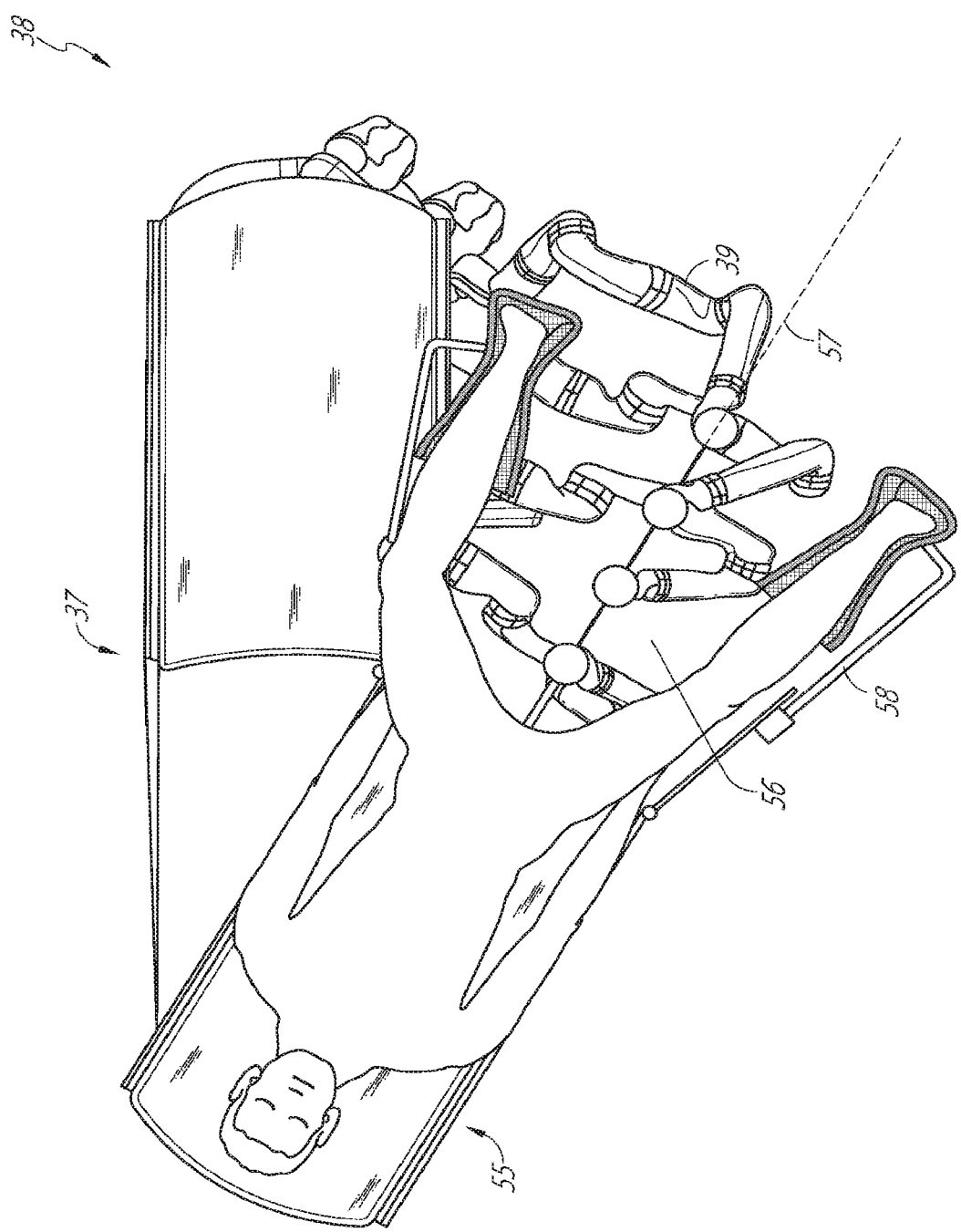
FIG. 8 illustrates an embodiment of a table-based robotic system configured for a ureteroscopy procedure.

FIG. 8 illustrates an embodiment of a robotically enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
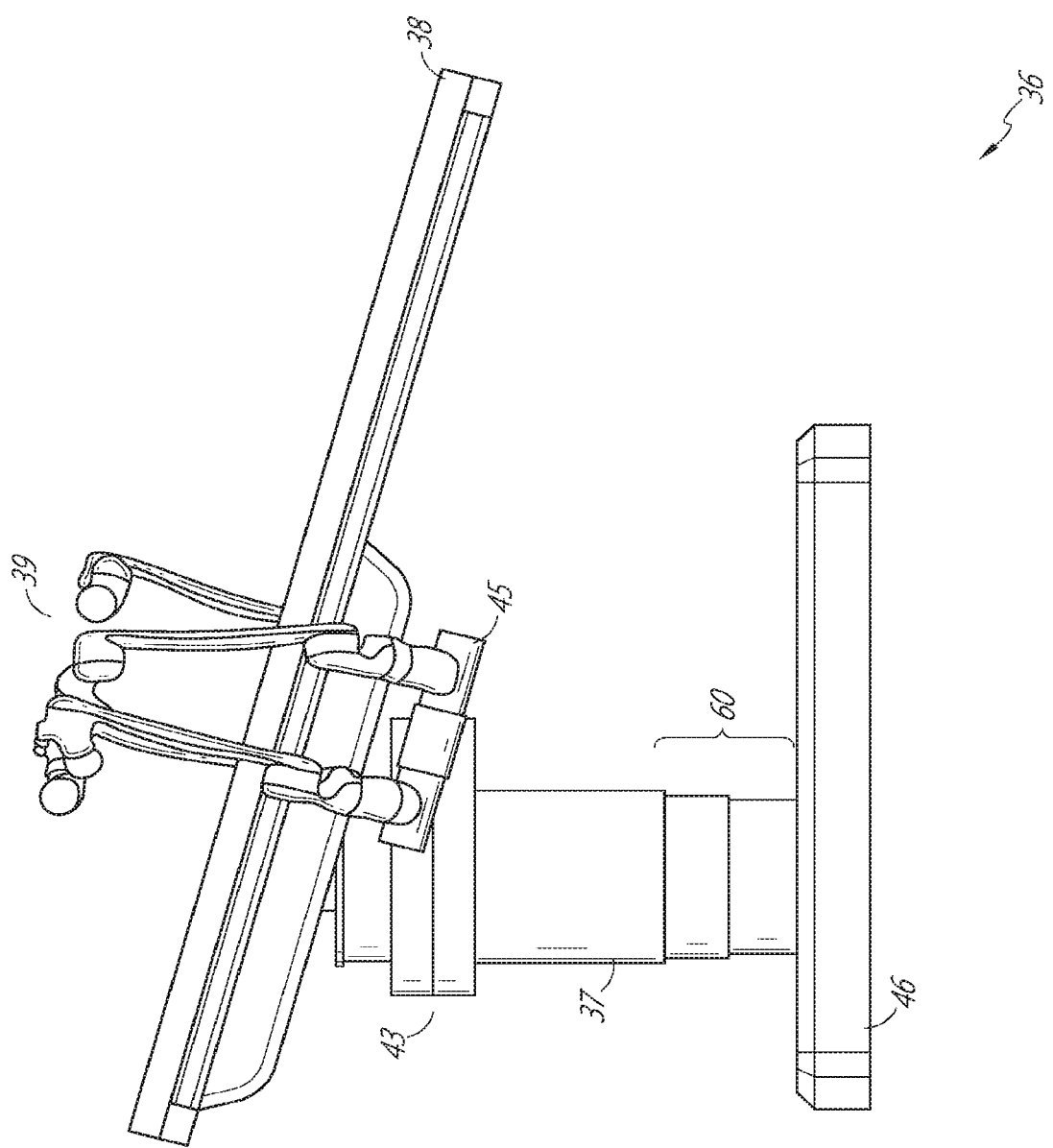
FIG. 10 illustrates an embodiment of the table-based robotic system of FIGS. 5-9 with pitch or tilt adjustment.

To accommodate laparoscopic procedures, the robotically enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
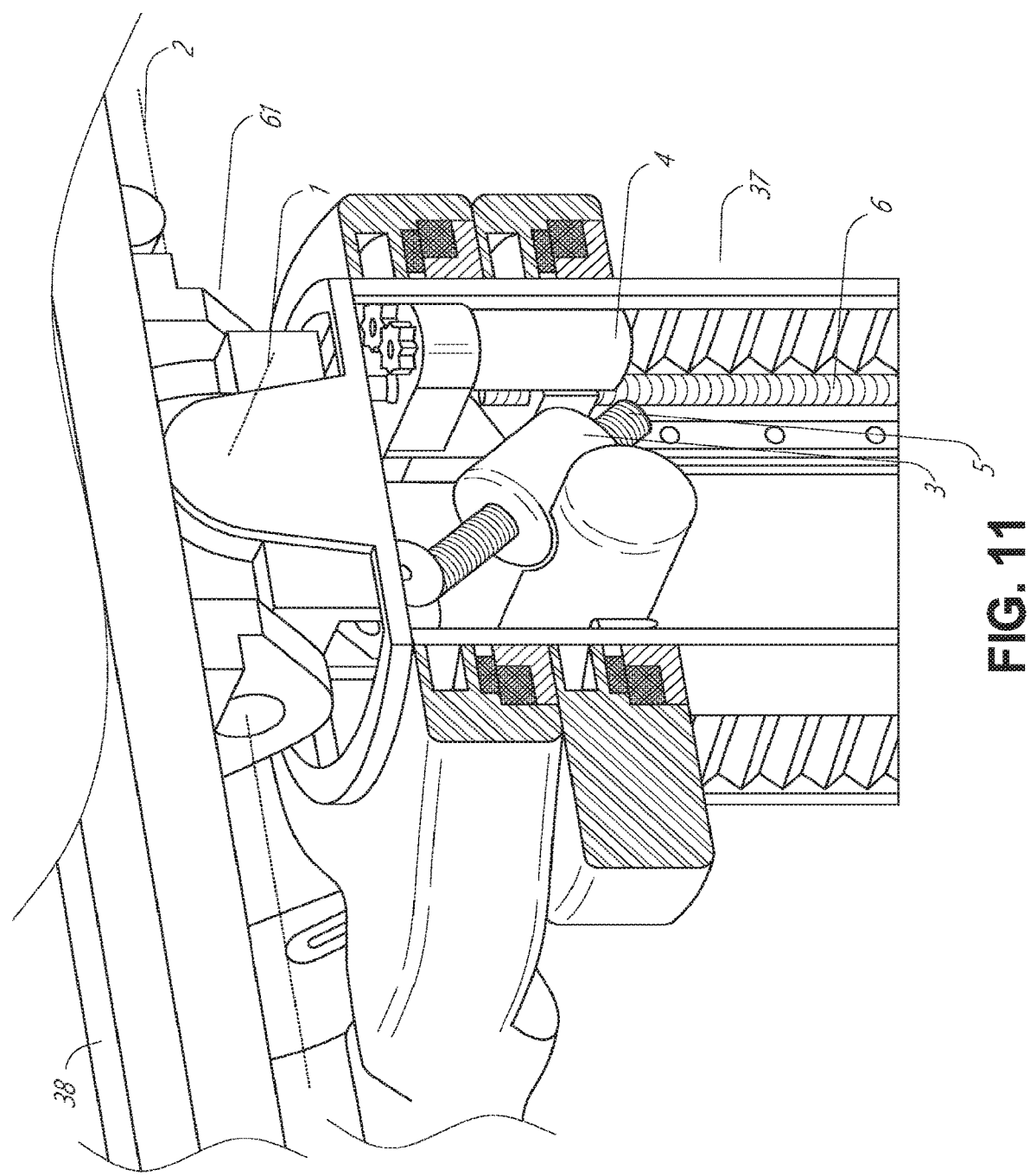
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
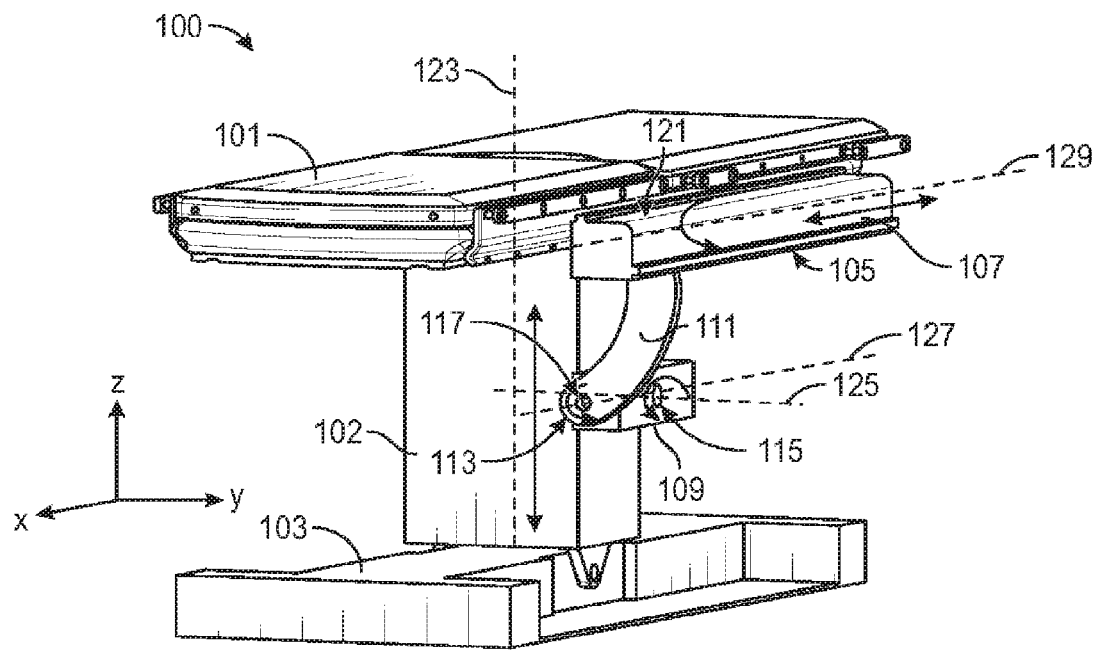
FIG. 12 illustrates an alternative embodiment of a table-based robotic system.
Figure 13:
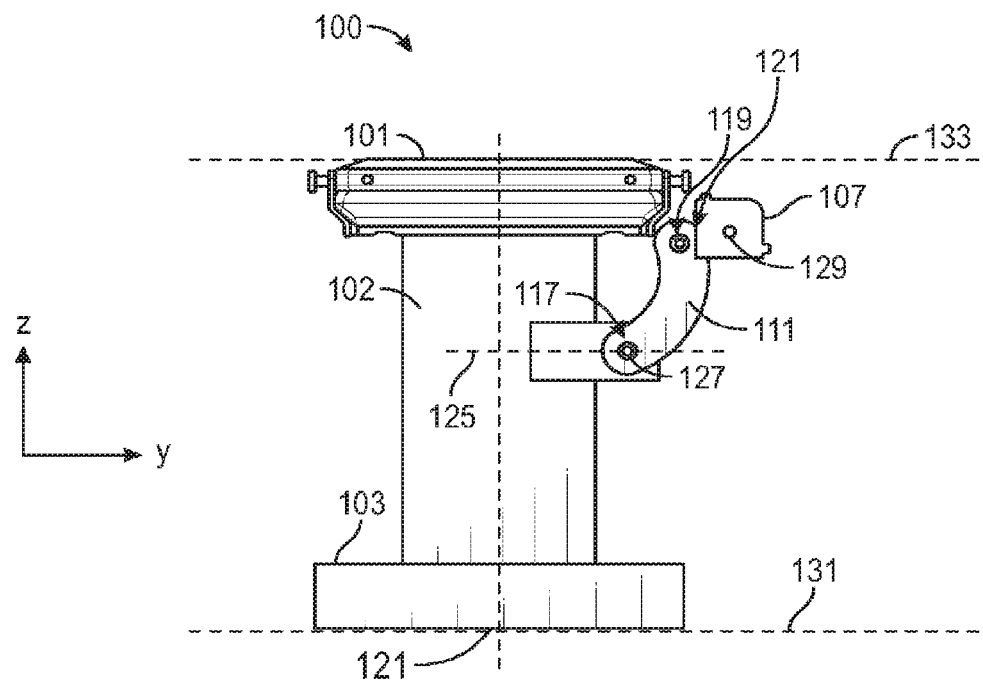
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
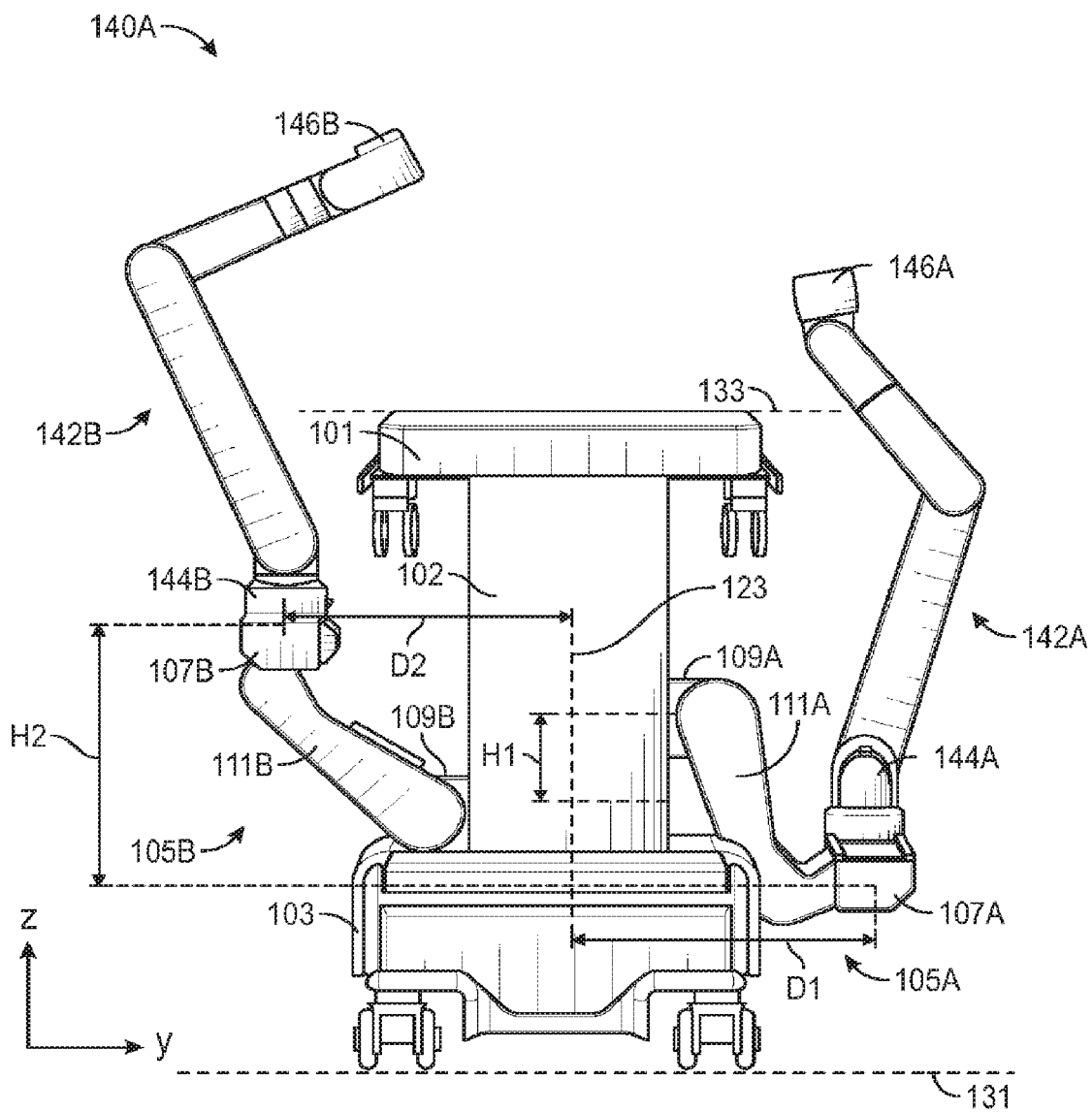
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (I-degree of freedom including elbow pitch), a shoulder (2-degrees of freedom including shoulder pitch and yaw), and base 144A, 144B (I-degree of freedom including translation). In some embodiments, the insertion degree of freedom can be provided by the robotic arm 142A, 142B, while in other embodiments, the instrument itself provides insertion via an instrument-based insertion architecture.

Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
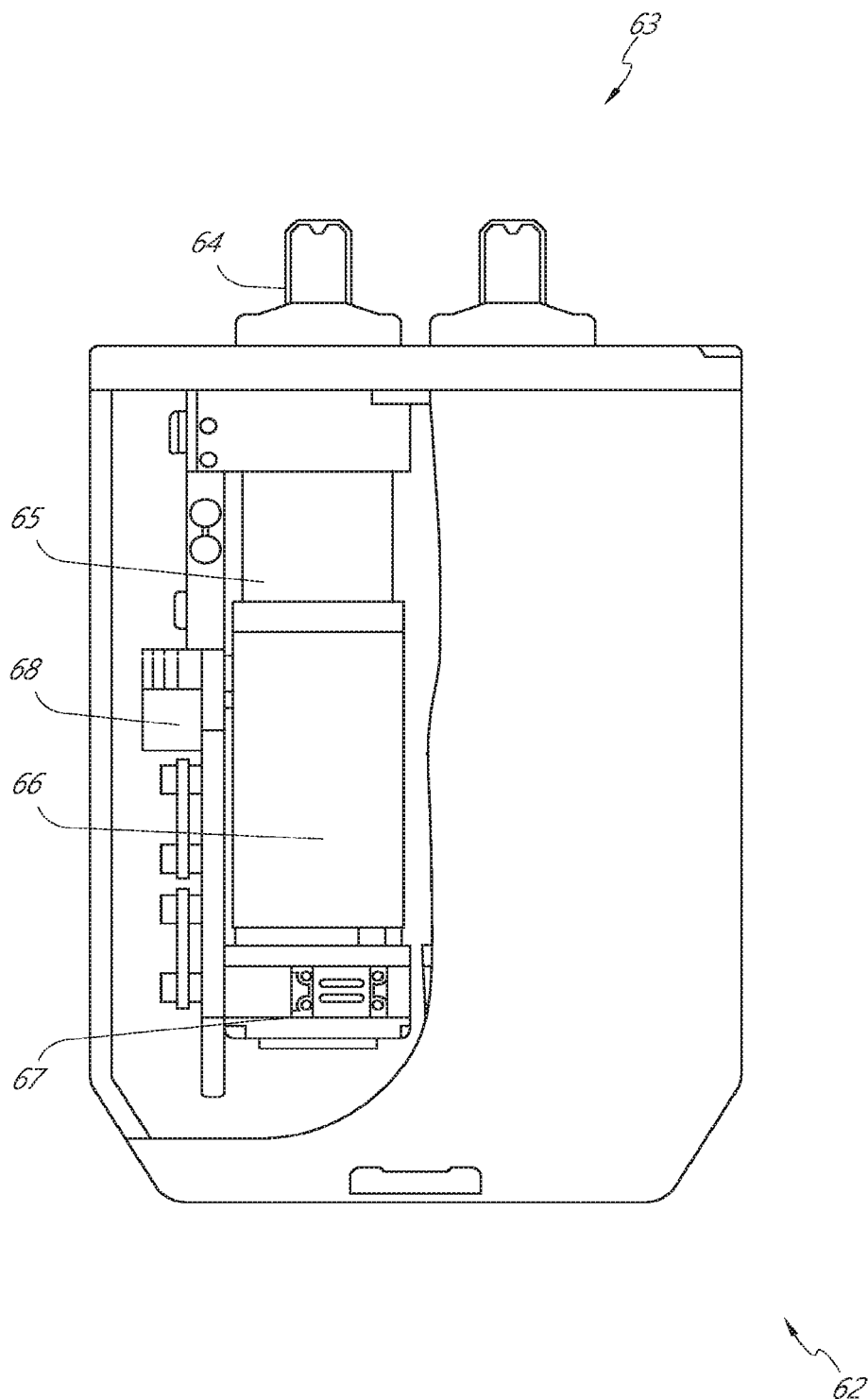
FIG. 15 illustrates an exemplary instrument driver.

FIG. 15 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).
Medical Instrument.

Figure 16:
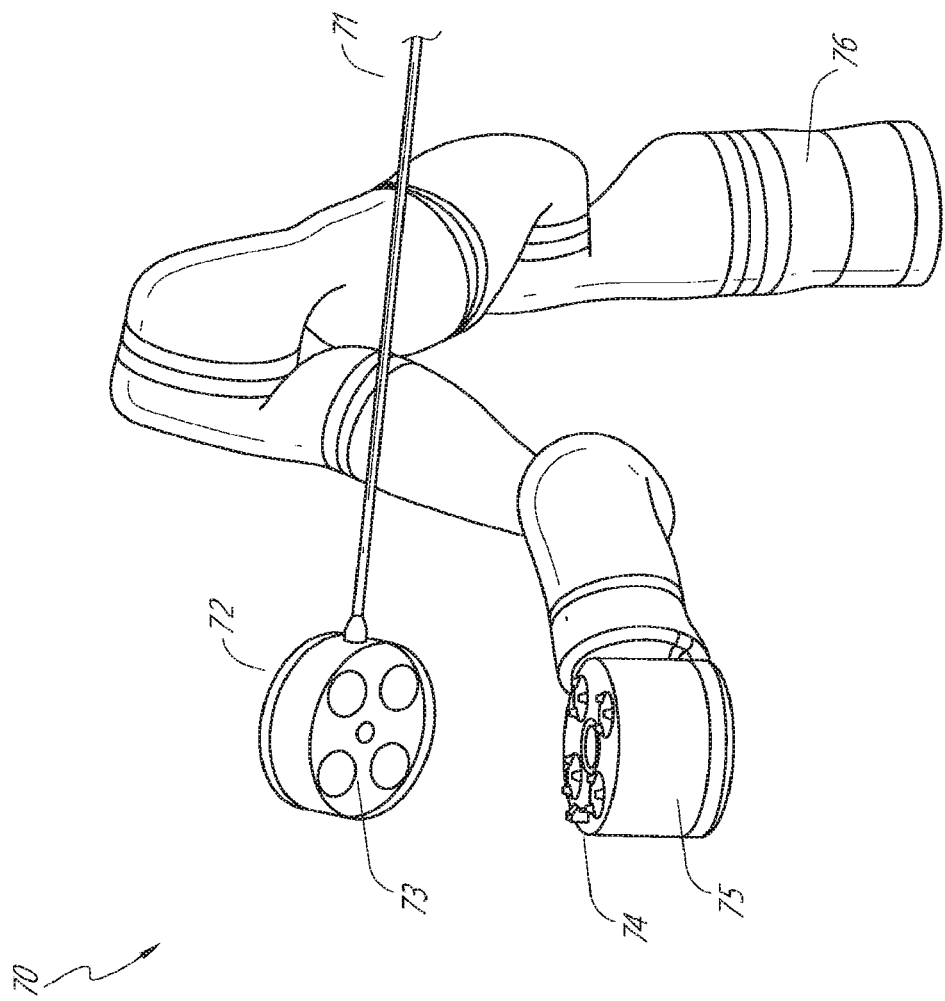
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space.

Relatedly, the distal tip may also include ports for light sources for illuminating the anatomical space when using the camera.

In the example of FIG. 16, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft during an endoscopic procedure.

Figure 17:
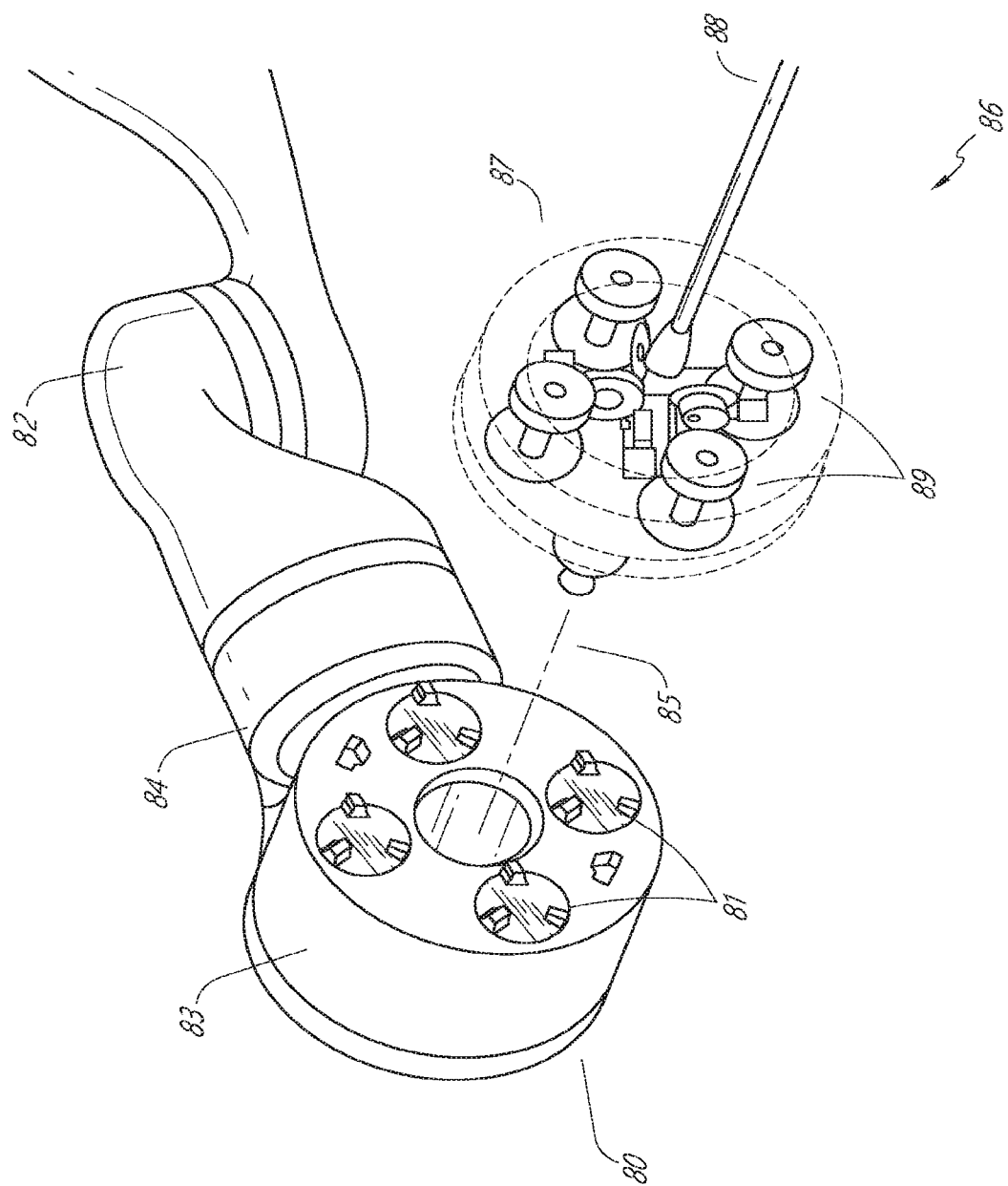
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
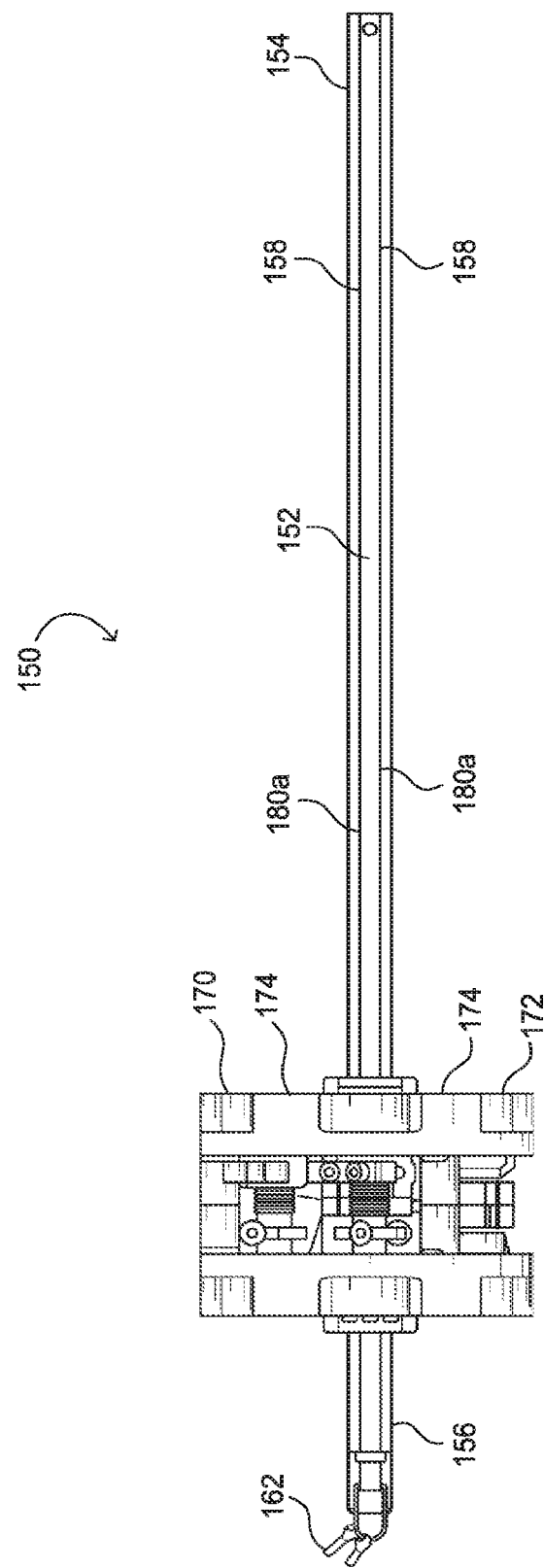
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
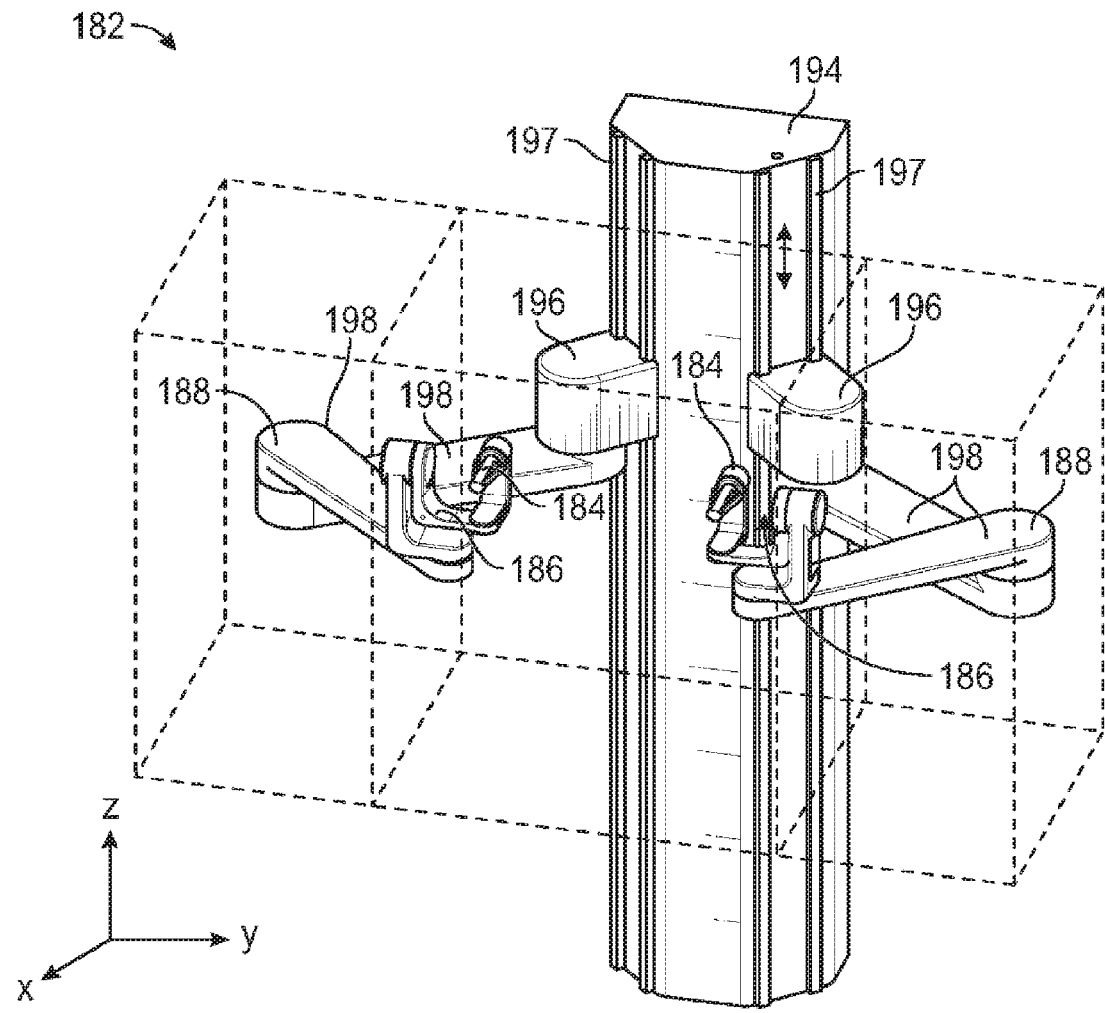

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
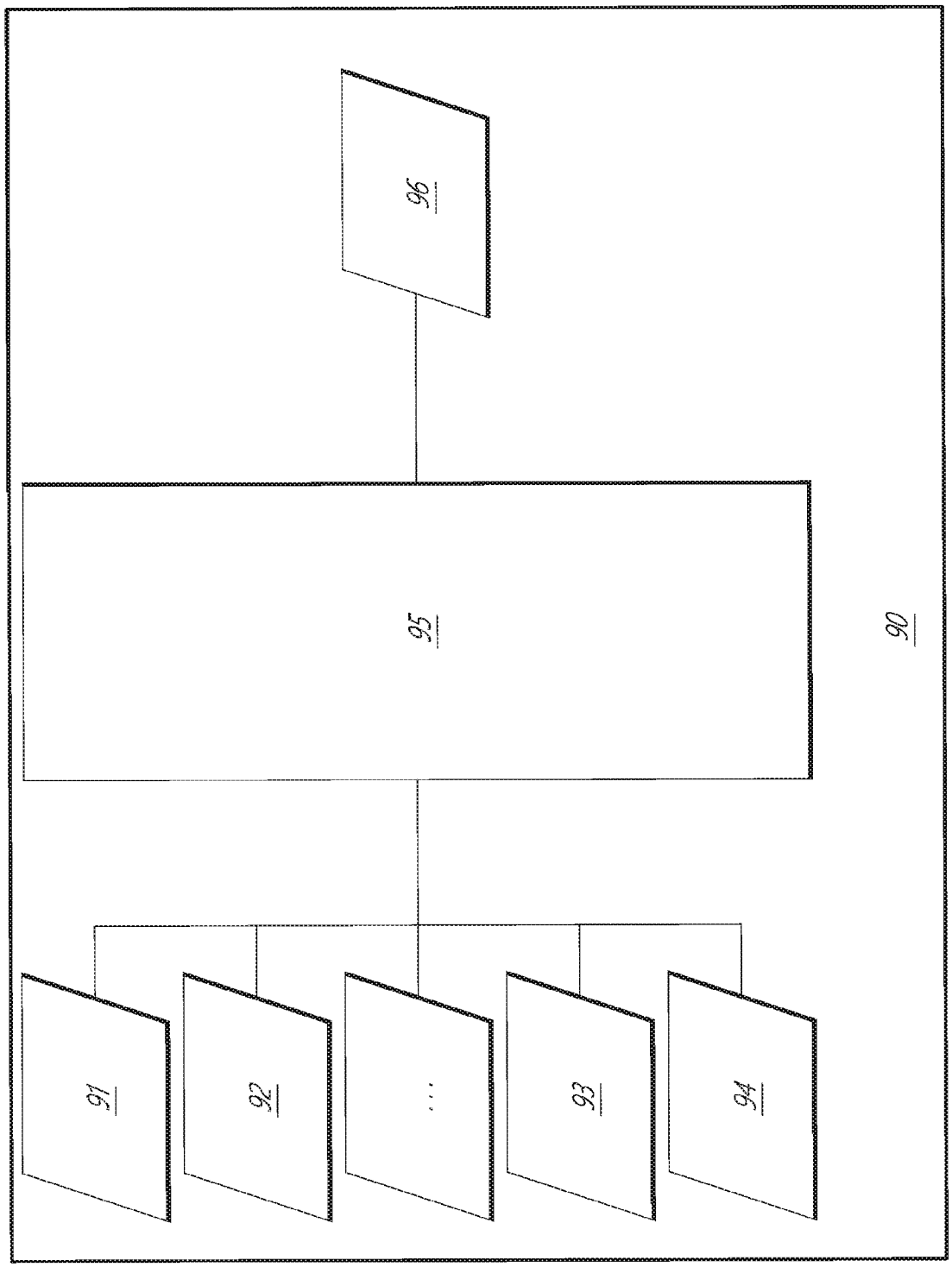
FIG. 20 depicts a block diagram illustrating a localization system that estimates a location of one or more elements of the robotic systems of FIGS. 1-10, such as the location of the instrument of FIGS. 16-18, in accordance with an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

Introduction to a Tissue Sealing and Cutting Device.

This application relates to multi-functional instruments that can be used in various types of surgery, including but not limited to laparoscopic, full open, mini-open and minimally invasive surgeries. In some embodiments, the multi-functional instrument can serve as both a tissue/vessel sealer and a cutter. The cutter, as described in the embodiments herein, may also be referred to as a rotary cutter, a blade, a cutting blade, a cutting element, or a cutting mechanism. The tissue sealer works by using grips/jaws to clamp down on tissue with high pressure to stop blood flow in blood vessels and tissue bundles. Energy is then passed through the jaws to heat the tissue so that the molecular bonds of the vessel walls join and fuse the vessel closed. A mechanical cutting means is then used to transect the vessel. The present application describes different embodiments of a multi-functional instrument that serve as both a tissue sealer and a cutter with novel cutting mechanisms. In some embodiments, the multi-functional instrument includes one or more cutters that can move in a translational direction. In other embodiments, the multi-functional instrument includes one or more cutters that can move in a rotary direction.

Figure 21:
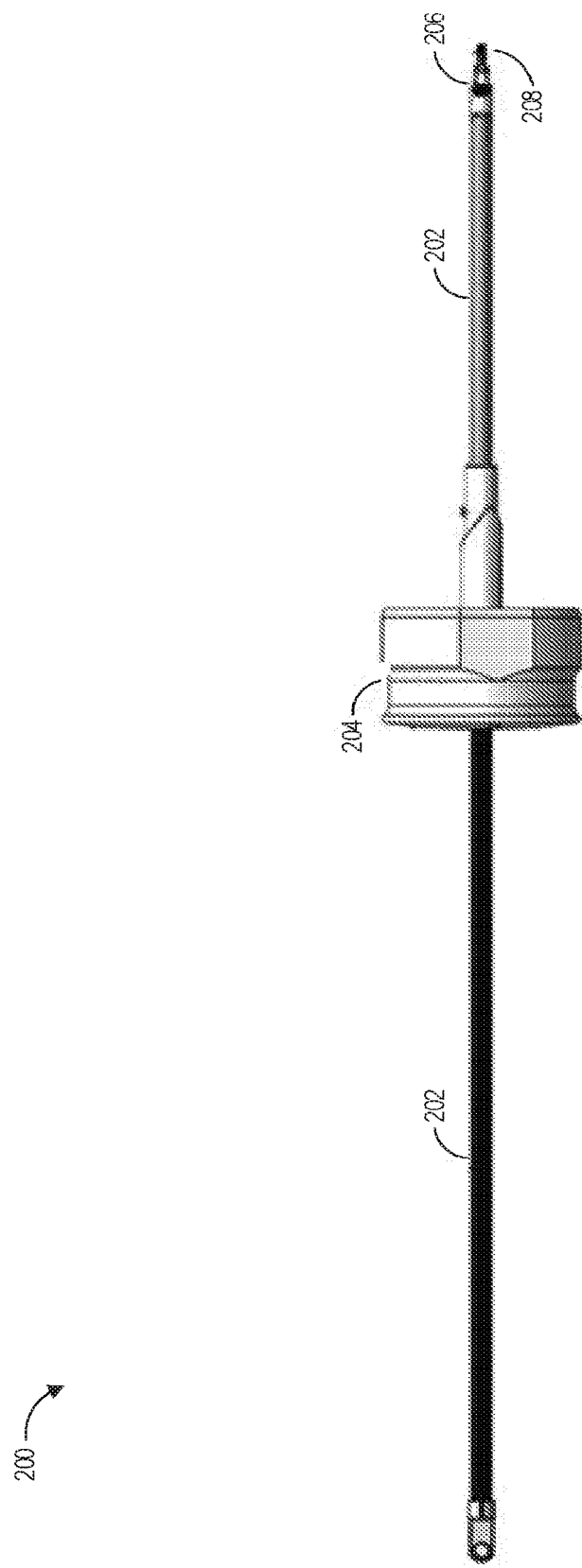
FIG. 21 illustrates a side view of a surgical instrument.

FIG. 21 illustrates a side view of an embodiment of a multi-functional surgical instrument 200. The surgical instrument 200 can include an elongate shaft 202, a handle 204, a wrist 206, and an end effector 208. The end effector can also be referred to herein as a surgical effector 208.

FIGS. 22A-C illustrate a first embodiment of the surgical effector 208. FIG. 22A is a perspective view of the surgical effector 208; FIG. 22B illustrates a side view the surgical effector 208; and FIG. 22c illustrates a front view of the surgical effector 208. The surgical instrument 200 can include distal pulleys 224, which will be described in more detail below. The wrist 206 can be positioned proximal to the surgical effector 208 and can include a proximal clevis 250 and a distal clevis 260. The proximal clevis 250 can be configured to be mechanically attached to the distal end of the elongate shaft 202 (shown in FIG. 21). The wrist 206 can be mechanically coupled to the surgical effector 208, such that the wrist 206 can be used to couple the surgical effector 208 to the shaft 202. The distal clevis 260 can be located distally in relation to the proximal clevis 250. Likewise, the surgical effector 208 can be located distally in relation to the distal clevis 260.

The distal clevis 260 may be mechanically coupled to the surgical effector 208 by the distal joints 222. The proximal clevis 250 may be mechanically coupled to the distal clevis 260 by the proximal joints 220. The distal and proximal joints 222, 220 allow the wrist 206 to articulate. In some embodiments, the proximal clevis 250 forms a first type of joint with the distal clevis 260, while the distal clevis 260 forms a second type of joint with the first and second jaw halves of the surgical effector 208. In some embodiments, the first type of joint is a rolling cycloid based joint for pitch, while the second type of joint is a pin-based joint for yaw motion. The distal clevis 260 can form in part distal joints 222 about which the surgical effector 208 can rotate. Similarly, the proximal clevis 250 can form in part proximal joints 220 about which the wrist 206 can pivot with respect to the elongate shaft 202. The proximal joints 220 may be formed by the intersection or connection of the proximal end of the distal clevis 260 with the distal end of the proximal clevis 250.

The instrument 200 can include one or more distal pulleys 224 that in certain embodiments can be shared by at least two cable segments. By sharing at least two cable segments on the pulley 224, the size of the surgical instrument 200 can be reduced by eliminating the number of pulleys on the surgical instrument 200. For example, in certain embodiments, the outer diameter of the surgical instrument 200 can be reduced to less than 6 mm, such as between 5 mm and 6 mm. The surgical instrument 200 described herein can also include passages 252, 262 (shown in FIGS. 22A-C and 23A-B) to receive and direct the cable segments through the surgical instrument 200. These passages 252, 262 can be used instead of or in addition to pulleys, which can further reduce the size of the surgical instrument 200. In some embodiments, the passages 252, 262 can be found within a distal clevis 260 of the instrument 200.

Although the cable segments are not illustrated in FIGS. 22A-C, shown, the wrist 206 can include one more cable segments. In some embodiments, the wrist 206 can include four cable segments. In some embodiments, the cable segments can be portions of the same cable. The cable segments may be tension cables. The cable segments can extend through the elongate shaft 202 (shown in FIG. 21), extend through the proximal clevis 250, and/or extend through the distal clevis 260. In some embodiments, the cable segments can extend through the walls of the elongate shaft 202 and/or the wrist 206, including the distal clevis 260 and the proximal clevis 250. As shown in FIGS. 22A-C and as mentioned above, the surgical instrument 200 described herein can also include passages 252, 262 to receive and direct the cable segments through the surgical instrument 200. These passages 252, 262 can be used can further reduce the size of the surgical instrument 200.

As mentioned above and shown in FIGS. 22A-C and 23A-B, the proximal clevis 250 can include proximal passages 252 and the distal clevis 260 can have distal passages 262. Each of the cable segments can be configured to engage the proximal passages 252 and distal passages 262. The proximal clevis 250 can include the proximal passages 252, as shown in FIGS. 22A-C and 23A-C, that redirect the cable segments through the proximal clevis 250 towards the distal clevis 260. Similarly, the distal clevis 260 can include the distal passages 262, as shown in FIGS. 22A-C and 23A-C, that redirect the cable segments through the distal clevis 260 towards the surgical effector 208. Each of the cable segments can be configured to engage the proximal passages 252 and distal passages 262. The proximal passages 252 and the distal passages 262 can be configured to reduce, or in some cases, prevent tangling or shearing of the cable segments. The proximal passages 252 and the distal passages 262 can also be configured to reduce the amount of friction between the cable segments and the proximal clevis 250 or the distal clevis 260, respectively.

As best seen in FIG. 22C, the distal pulleys 224 can include two pulleys 224a, 224b that are each shared by two cable segments (not illustrated) as noted above. The cable segments can engage at least a portion of the distal pulleys 224. FIGS. 23A and 23B show a top view and a side view of the wrist 206, showing additional detail of the distal pulleys 224. In the present embodiment, the distal pulleys 224 can include two pulleys 224a, 224b; however, in other embodiments, the distal pulleys 224 each include two or more pulleys (such as three, four, five or six). The two pulleys 224a, 224b of the distal pulleys 224 can be adjacent to one another and aligned along the yaw axis 292. In certain embodiments, each of the two pulleys 224a, 224b can be offset from a central axis 294 of the wrist 206 such that a working lumen could be positioned between the pulleys 224a, 224b. In some embodiments, the two pulleys 224a, 224b of the distal pulleys 224 can be adjacent to one another and aligned along the yaw axis 292.

With continued reference to FIGS. 22C and 23A-C, a first cable segment and a second cable segment can be routed to engage the first distal pulley 224a, while a third cable segment and a fourth cable segment can be routed to engage the second distal pulley 224b. In some embodiments, the independent cable segments move in equal but opposite amounts about the distal pulleys 224. In some embodiments, neither of the cables or cable segments that are shared around each distal pulley 224a, 224b engage with or intersect with one another. In some embodiments, neither of the cables or cable segments that are shared around the distal pulley 224 are directly connected to one another, such as via a crimp. Such pulley sharing configuration allows the wrist 206 to have less pulleys for the same degree of freedom of movement, which can allow the wrist 206 and the elongate shaft 202 to have a smaller outer diameter (e.g., less than 6 mm in certain embodiments, such as between 6 mm and 5 mm in certain embodiments) and/or for additional components to be added to the surgical instrument in the place of the removed pulleys such as, for example, the working lumen that can extend between the distal pulleys 224a, 224b.

The surgical effector 208 can actuate in multiple degrees of movement. In the illustrated embodiment, the surgical effector 208 can have degrees of movement about a pitch axis 290 and a yaw axis 292, as illustrated in FIGS. 22A and 23A-B. In some embodiments, the instrument including the surgical effector 208 can have N+1 cable segments and N degrees of freedom of movement. For example, the instrument can include wrist 206 capable of at least two degrees of freedom, wherein the wrist is pivotable around the pitch axis 290 and the yaw axis 292. In some embodiments the surgical instrument including the surgical effector 208 can comprise at least four cable segments to control at least three degrees of freedom, such as, for example, pitch, yaw and grip.

FIGS. 22A-22C illustrate the surgical effector 208 in an example "neutral" state, e.g., the first yaw angle 272, the second yaw angle 274, and the pitch angle 270 are not offset from the central axis 294, with no cable segments being advanced or retracted. The first yaw angle 272 can be manipulated by advancing/retracting the first cable segment and retracting/advancing the second cable segment.

The surgical effector 208 of the illustrated embodiment includes a first jaw half 208a and a second jaw half 208b that can be operatively connected to the first pulley 224a and the second pulley 224b of the distal pulleys 224, respectively. Thus rotation of the first pulley 224a of the distal pulleys 224 about the yaw axis 292 causes rotation of the first jaw half 208a about the yaw axis 292. Similarly, rotation of the second pulley 224b of the distal pulleys 224 about the yaw axis 292 causes rotation of the second jaw half 208b about the yaw axis 292. FIGS. 22A-C illustrate the two jaw halves 208a, 208b in a closed position. FIGS. 23A-B illustrate the two jaw halves 208a, 208b in an open position where the two jaw halves 208a, 208b are separated from each other.

In some embodiments, the yaw motion of each jaw half 208a, 208b of the surgical effector 208 can be actuated by a combination of cable segment actuations to rotate the distal pulleys 224. For example, the lengthening of the first cable segment matched with a shortening of the second cable segment can cause the first jaw half 208a to rotate about the yaw axis 292 in a first direction. Similarly, the lengthening of the second cable segment matched with a shortening of the first cable segment can cause the first jaw half 208a to rotate about the yaw axis 292 in a second direction, where the second direction is opposite the first direction.

The second jaw half 208b can be actuated by a combination of cable segment actuations of the third cable segment and fourth cable segment in a similar manner as the first jaw half 208a as described above. For example, the third cable segment can have tension applied, such as pulling, to actuate the second jaw half 208b of the surgical effector 208 in a first direction about the yaw axis 292. The fourth cable segment can have tension applied, such as pulling, to actuate the second jaw half 208b of the surgical effector 208 in a second direction about the yaw axis 292, where the second direction is opposite the first direction.

Figure 23C:
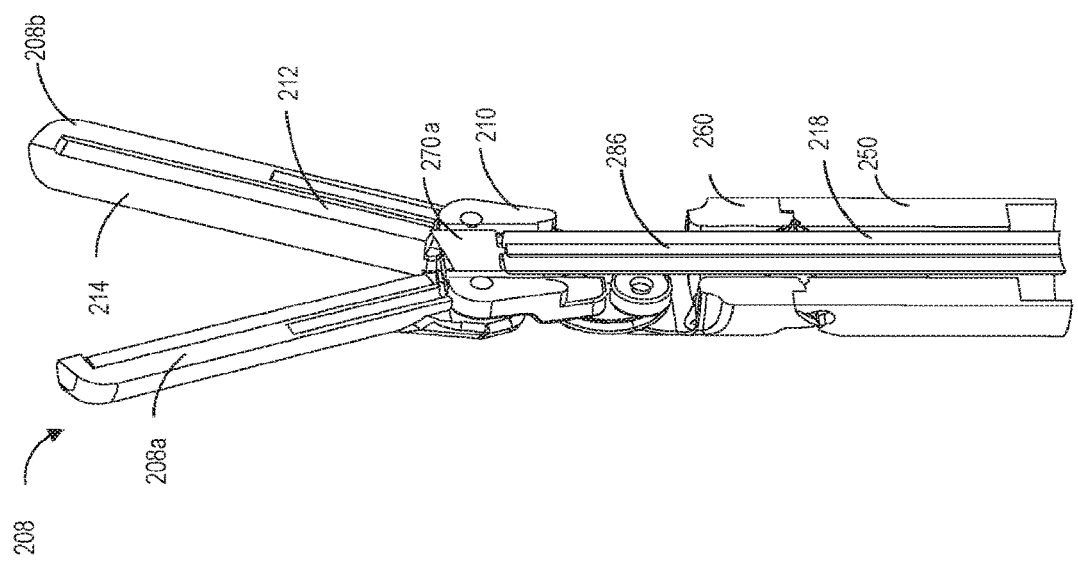
FIG. 23C illustrates a cross sectional view of the first embodiment of the surgical effector shown in FIG. 23A.

FIGS. 23A-C illustrates the two jaw halves 208a and 208b of the surgical effector 208 rotated at the first yaw angle 272 and the second yaw angle 274 about the yaw axis 292. FIGS. 23A-C demonstrate the potential yaw movement of the surgical effector 208 in accordance with some embodiments. Although the cable segments are not shown in FIGS. 23A-B, advancing the first cable segment and/or retracting the second cable segment engaging the first distal pulley 224a causes the first jaw half 208a to rotate about the yaw axis 292 such that the first yaw angle 272 increases. On the other hand, retracting the first cable segment and/or advancing the second cable segment engaging with the first distal pulley 224a causes the first jaw half 208a to rotate about the yaw axis 292 such that the first yaw angle 272 decreases. Similarly, the second yaw angle 274 can be manipulated by advancing/retracting the third cable segment and retracting/advancing the fourth cable segment. Advancing the third cable segment and/or retracting the fourth cable segment engaging with the second distal pulley 224b causes the second jaw half 208b to rotate about the yaw axis 292 such that the second yaw angle 274 increases. On the other hand, retracting the third cable segment and/or advancing the fourth cable segment engaging with the second distal pulley 224b causes the second jaw half 208b to rotate about the yaw axis 292 such that the second yaw angle 274 decreases. As shown in FIG. 23A-C, the two jaw halves 208a, 208b of the surgical effector 208 can be rotated about the yaw axis 292 at the distal joints 222 independently, such that the two jaw halves 208a, 208b can be rotated away from each other in opposite directions.

Although the first and second jaw halves 208a, 208b are described herein as examples to describe the rotation of the surgical effector 208, features of the surgical effector 208 described above may also be used in combination with first and second jaw halves of the other embodiments described below such as 208c, 208d, 208e, 208f, 208g, 208h, or 208i, 208j, as described more below.

The cable segments may be further configured so that retracting or advancing a cable segment can actuate the surgical effector 208 to move in a second degree of motion about the pitch axis 290. The first cable segment and the second cable segment can be routed on a first side of the distal clevis 260, while the third cable segment and the fourth cable segment 236 can be routed on a second side of the distal clevis 260. The first cable segment and third cable segment can be routed on a first side of the proximal clevis 250, while the second cable segment and fourth cable segment can be routed on a second side of the proximal clevis 250. In some embodiments, pitch motion of the surgical effector 208 can be actuated by a combination of cable segment actuations, such as an even lengthening of a pair of cable segments matched with an even shortening of another pair cable segments, which can cause the distal clevis 260 to rotate about the pitch axis 290.

The pitch angle of the surgical effector 208 can be manipulated by retracting/advancing the first cable segment and the second cable segment and advancing/retracting the third cable segment and the fourth cable segment to rotate about the pitch axis 290 such that the pitch angle increases or decreases. In some embodiments, pitch motion of the surgical effector 208 can be actuated by a combination of cable segment actuations, such as applying tension (such as pulling) of the first and second cable segments, matched with an even slacking of the third and fourth cable segments, which can cause the distal clevis 260 to rotate about the pitch axis 290 about the proximal joints 220, in a first direction. Similarly, the pitch motion of the surgical effector 208 can be actuated by a combination of cable segment actuations, such as applying tension of the third and fourth cable segments matched with an even shortening of the first and second cable segments, which can cause the distal clevis 260 to rotate about the pitch axis 290 about the proximal joints 220 in a second direction.

In other embodiments, the surgical instrument 200 may include one or more proximal pulleys (not shown) that can be located distally in relation to the distal pulleys 224. The proximal pulleys can actuate a degree of movement about the pitch axis 290.

As described previously, the rotation of the distal pulleys 224 is caused by retracting or advancing the cable segments. Similarly, the pitch motion is caused by retracting and advancing the cable segments as described above. In certain embodiments, an input controller can be coupled to each of the four cable segments. In such arrangements, the first input controller can advance/retract the first cable segment; the second input controller can advance/retract the second cable segment; the third input controller can advance/retract the third cable segment; and the fourth input controller can advance/retract the fourth cable segment.

Gripper and Sealer

Referring again to FIGS. 23A-D, the surgical effector 208 can act as a grasper or gripper. As previously discussed, the first and second jaw halves 208a, 208b may rotate towards each other or away from each other, between the opened and closed position. The first and second jaw halves 208a, 208b may be rotated, between the open position, as shown in FIGS. 23A-D, and the closed position, as shown in FIGS. 22A-C. As shown in FIGS. 23A-B, the first and second jaw halves 208a, 208b can be in an open position where the distal ends of the two jaw halves 208a, 208b are separated from each other or are positioned away from each other. The first and second jaw halves 208a, 208b in the open position may be positioned around tissue to receive tissue within a patient. The first and second jaw halves 208a, 208b may be rotated about the yaw axis 292 in a closed position where the first and second jaw halves 208a, 208b are configured to clamp tissue to grasp or grip tissue within a patient. The first and second jaw halves 208a, 208b need not be completely closed to grip the tissue, when tissue is positioned between two jaw halves 208a, 208b. As described above, the first and second jaw halves 208a, 208b may serve as grippers to clamp down on tissue. In some embodiments, the first and second jaw halves 208a, 208b may grip tissue with high pressure to stop blood flow in blood vessels and tissue bundles. The first and second jaw halves 208a, 208d may have an interior face 214 structured or configured to engage tissue.

Each of the first and second jaw halves 208a, 208b may include one or more bipolar electrodes on the interior faces 214 of the first and second jaw halves 208a, 208b. In a bipolar configuration, bipolar electrodes are located in the interior faces 214 of the jaw halves 208a, 208b. In some embodiments, each of the jaw halves 208a, 208b includes a set of one or more electrically isolated bipolar electrodes. In other embodiments, one jaw half 208a, 208b can contain both sets of electrodes. The first and second jaw halves 208a, 208b may include conducting material positioned on the face 214 of the first and second jaw halves 208a, 208b to form the electrodes. In an alternative configuration, the instrument is a monopolar instrument.

In some embodiments, the electrodes are "C-shaped" and are mirror reflected. The electrodes each extend around a perimeter of a slot 212 that provides clearance for a blade or wire. In some embodiments, the electrodes for the instrument 200 are located on the interior faces 214 of each of the two jaw halves 208a, 208b. These electrodes can be kept isolated from each other, regardless of the position of the two jaw halves 208a, 208b. In some embodiments, a plastic insulating layer between the jaw halves 208a, 208b and electrodes prevents the wrist 206 from forming a conductive path to one or both electrodes. Physical spacers on and around the electrodes can prevent the electrodes from contacting when the jaw halves 208a, 208b are in the closed position, so that the bipolar energy will not be shorted, and such that it will pass through the tissue clamped by jaw halves 208a, 208b. In other embodiments, sealing is accomplished via monopolar energy. In some embodiments, sealing is accomplished via bipolar energy through the electrodes positioned on the interior faces 214 of each jaw half 208a, 208b.

Each electrode may be a conducting element that is made of material that conducts electricity well, such as copper or steel. In some embodiments, the electrode may be coated with a biocompatible material that prevents the electrode from sticking or adhering to tissue, such as a metal with a high nickel content at the surface. The electrode may be connected to a conducting wire that carries energy to the electrode from a power source, such as a generator. The electrode may be isolated from the remainder of the jaw half 208a, 208b with nonconducting material.

As described above, the jaw halves 208a, 208b, may serve as grippers to receive and clamp tissue. Also, as described above, the instrument 200 may include a cutting mechanism such as a blade or cutter to transect or cut the vessel gripped by the first and second jaw halves 208a, 208b.

Although the first and second jaw halves 208a, 208b are described herein as examples to describe the rotation of the surgical effector 208, including the electrodes located on the interior faces 214 of the two jaw halves 208a, 208b, the features of the surgical effector 208 described above may also be included in the first and second jaw halves of the other embodiments described such as 208c, 208d, 208e, 208f, 208g, 208h, or 208i, 208j, as described more below. Similarly, while the first and second jaw halves 208a, 208b are described above as examples of the operation of the electrodes positioned on the interior faces 214 of the jaw halves 208a, 208b for sealing, the features described above may also be included in the first and second jaw halves of the other embodiments described such as 208c, 208d, 208e, 208f, 208g, 208h, or 208i, 208j, as described more below Longitudinal Blade.

Referring again to FIGS. 22A-C and FIG. 23A-D, the instrument 200 may include a blade 270a which can be deployed longitudinally. In particular, FIG. 23C illustrates a cross sectional view of the surgical effector shown in FIG. 23A which illustrates the blade 270a in additional detail. As the blade 270a is actuated to move longitudinally along the axis of the instrument 200, the blade 270a may cut tissue positioned between the first and second jaw halves 208a, 208b. In some embodiments, the blade 270a is controlled actively, while in other embodiments, the blade 270a can be controlled passively. In some embodiments, the blade 270a can be deployed through the proximal clevis 250 and/or the distal clevis 260. In the illustrated embodiment, the blade 270a is a rectangular blade. In other embodiments, the blade 270a may be in the form of scissors, arced scythe, serrated blade, razor, or another type of cutting feature, that can be deployed to cut tissue. In the illustrated embodiment, the blade 270a can be deployed via longitudinal motion. In other embodiments, the blade 270a can be deployed via translation along a different axis (for example, perpendicular to a longitudinal axis of the instrument), rotational motion or a combination thereof. In some embodiments, the blade 270a can be in-line or offset from a central axis 294 of the instrument 200. The blade 270a may be also be referred to as a cutter, a cutting blade, a cutting element, or a cutting mechanism.

As described above, positioning the cable segments through the walls of the wrist 206 can allow for additional components to be added to the surgical instrument 200 without increasing the diameter of the instrument 200. For example, as best shown in FIG. 23C, a blade container 210 and/or a blade conduit 218 may be positioned within the working lumen of the surgical instrument 200. The blade container 210 defines a lumen through which the blade 270a can move. The blade container 210 extends at least partially between the first jaw half 208a and second jaw half 208b. The blade container 210 may receive the blade 270a. The blade container 210 may also serve as a shaft in which the blade 270a moves through. The blade container 210 may also allow the blade 270a to be stored away when not in use and may assist to deploy the blade 270a when actuated. In some embodiments, the blade container 210 includes two functions. A first function is to constrain/support the motion of the jaw halves 208a, 208b relative to one another as well as to the distal clevis 260. Due to this first function, the structure can be further extended to maintain a support or lumen structure for the blade 270a at a fixed distance from the jaw halves 208a, 208b.

With continued reference to FIG. 23C, the blade conduit 218 may be positioned within the working lumen of the surgical instrument 200. The blade conduit 218 may be positioned proximally relative to the blade container 210. The blade conduit 218 may also define a lumen through which the blade 270a can move. The blade conduit 218 may be flexible or rigid. The blade conduit 218 may receive a push shaft 286 and blade 270a. The push shaft 286 may be connected to the blade 270a and may actuate the blade 270a in moving in a proximal or distal direction. The blade conduit 218 may receive the push shaft 286 and the blade 270a and may serve as the lumen by which the blade 270a moves. The push shaft 286 may couple to the blade 270a which may be used to deploy the blade 270a through the blade conduit 218. The blade conduit 218 allows the blade 270a to be stored away when not in use and may assist to deploy the blade 270a when actuated.

As described previously, the first and second jaw halves 208a, 208b, may each include a central recess or slot 212 that may provide clearance to receive the blade 270a. When the first and second jaw halves 208a, 208b are in a closed position, the slot 212 of each jaw half 208a, 208b can form a space or enclosure through which the blade 270a moves through. In some embodiments, the slots 212 may further form a shaft, similar to the shaft formed by the blade container 210 and/or the blade conduit 218.

Rotary Cutter.

Figure 24B:
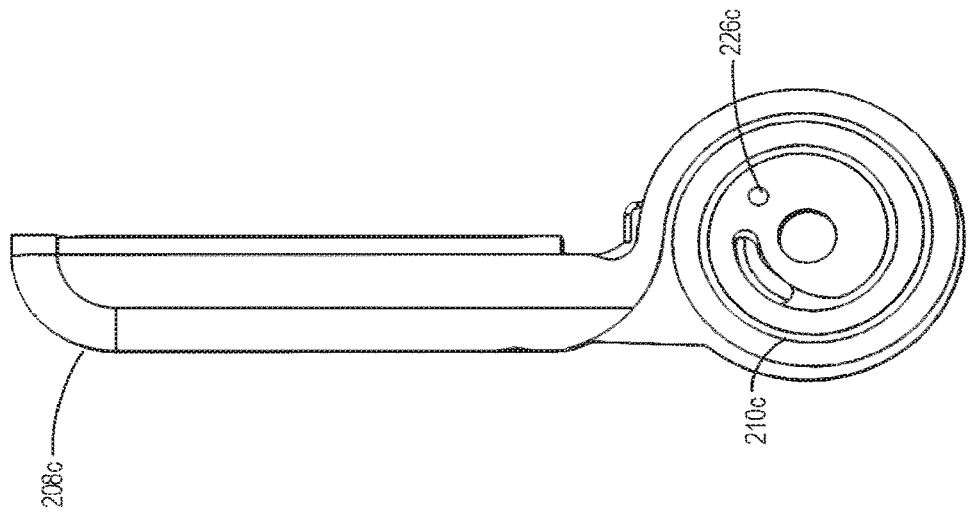
FIG. 24B illustrates a side view of the jaw half of the second embodiment of the surgical effector shown in FIG. 24A.
Figure 24A:
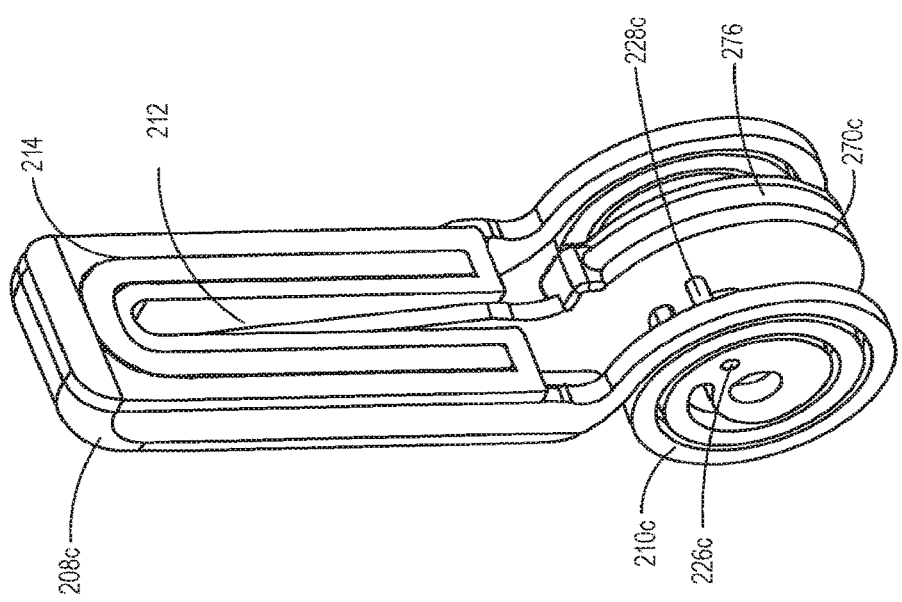
FIG. 24A illustrates a perspective side view of a Jaw half of a second embodiment of a surgical effector.

FIG. 24A illustrates a perspective side view of a first jaw half 208c of a second embodiment of a surgical effector 208, which can utilize a cutter that rotates. In some embodiments, the surgical effector 208 including the rotary cutter can be attached to the wrist and shaft shown in FIGS. 22A-23C. FIG. 24B illustrates a side view of the first jaw half 208c of the second embodiment of the surgical effector 208 shown in FIG. 24A. FIG. 24C illustrates a perspective rear view of the first jaw half 208c of the second embodiment of the surgical effector 208 shown in FIG. 24A. FIG. 24D illustrates a perspective front view of the first jaw half 208c of the second embodiment of the surgical effector 208 shown in FIG. 24A. The second jaw half 208d, shown in FIG. 26A-H, can be a mirror image of the first jaw half 208c, shown in FIGS. 24A-D. The rotary cutter, as described in the embodiments herein, may be also be referred to as a cutter, a blade, a cutting blade, a cutting element, or a cutting mechanism.

FIG. 25 illustrates a perspective side view of the rotary cutter 270c of the second embodiment of the first jaw half 208c. The rotary cutter 270c comprises a distal blade portion attached to a rounded base. The base of the rotary cutter 270c includes an opening or hole 284C through which a pin can be received therethrough, thereby coupling the rotary cutter 270c to one or more jaw members. In addition, the rotary cutter 270c includes one or more grooves 276 to receive cables or cable segments therein.

Figure 26G:
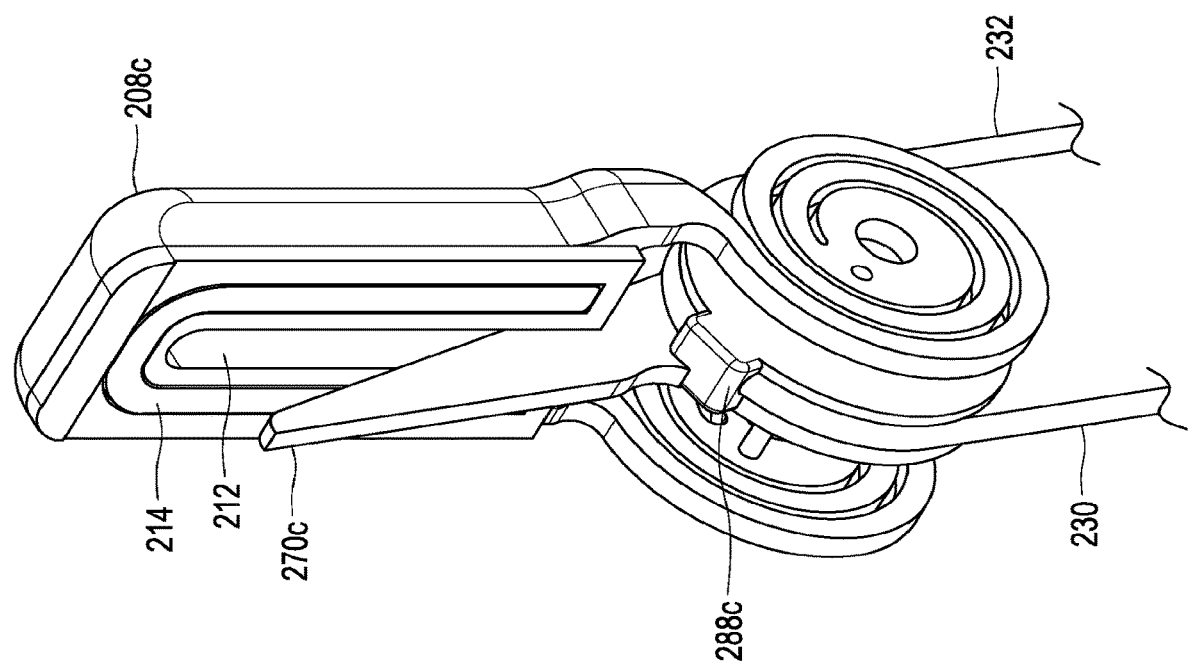
FIG. 26G illustrates a perspective view of a single jaw half and cutter of the second embodiment of the surgical effector shown in FIGS. 26A-F.

FIGS. 26A-H illustrates various views and positions of the second embodiment of the surgical effector 208 of FIGS. 24A-D, with certain components being shown as transparent. In particular, FIGS. 26A-C show a perspective view of the end effector in three configurations or positions—a first position with the first jaw half 208c and the second jaw half 208d in an open position (FIG. 26A), a second position with the first jaw half 208c and the second jaw half 208d in a closed position without actuation or deployment of the rotary cutters 270c, 270d (FIG. 26B), and a third position with the first jaw half 208c and the second jaw half 208d in a closed position with deployment of one or more rotary cutters 270c, 270d. FIGS. 26D-F show front views of the end effector, with FIG. 26D corresponding to the open position in FIG. 26A, FIG. 26E corresponding to the closed position with non-deployed rotary cutters in FIG. 26B, and FIG. 26F corresponding to the closed position with deployed rotary cutters in FIG. 26C. Advantageously, a single type of actuation mechanism (e.g., one or more cables) can cause the surgical effector 208 to move through each of the three positions or configurations shown in FIGS. 26A-C. In other words, a single type of actuation mechanism can initially move the jaw halves 208c, 208d from an open position to a closed position, and subsequently deploy the cutters 270c, 270d therein. This is due in part to the unique design of the end effector, as each of the jaw halves 208c, 208d are uniquely coupled to their respective cutters 270c, 270d, as described in more detail below.

The surgical effector 208 can include a first rotary cutter 270c positioned in a first jaw half 208c and a second rotary cutter 270d positioned in a second jaw half 208d. The second rotary cutter 270d may be a mirror image of the first rotary cutter 270c. The instrument 200 can include rotary cutters 270c, 270d that can each be deployed rotationally. In some embodiments, the surgical effector 208 can include a first rotary cutter 270c coupled to the first jaw half 208c. In some embodiments, the surgical effector 208 can also include the second rotary cutter 270d coupled to the second jaw half 208d. As shown in FIGS. 26A-F, the rotary cutters 270c, 270d can be arranged such that they are in a scissor-like configuration.

As described previously, the surgical effector 208 can act as a grasper or gripper. Similar to the first and second jaw halves 208a, 208b of the first embodiment, the jaw halves 208c, 208d of the second embodiment may similarly rotate towards and away from each other to receive and grasp tissue. FIGS. 26A and 26D illustrate the jaw halves 208c, 208d in the open position. FIGS. 26B and 26E illustrate the jaw halves 208c, 208d in the closed position with the cutters 270c, 270d not yet deployed or actuated. FIGS. 26C and 26F illustrate the jaw halves 208c, 208d in the closed position with the cutters 270c, 270d deployed or actuated. The jaw halves 208c, 208d can also include one or more electrodes for sealing as described above.

With continued reference to FIGS. 26A-H, each jaw half 208c, 208d may have a centerline cutout or recess 212 to accommodate a rotary scissor-type cutter 270c, 270d. The recesses 212 of the jaw halves 208c, 208d may also allow the rotary cutters 270c, 270d to be stored away when not in use, even if the jaws halves 208c, 208d are being used to grasp tissue. In some embodiments, each rotary cutter 270c, 270d can be deployed from each recess 212 of each jaw half 208c, 208d. Similar to the jaw halves 208c, 208d, the rotary cutters 270c, 270d can be actuated and rotate towards each other or away from each other, between the first and second positions.

In some embodiments, the first and second rotary cutters 270c, 270d can be in a first position where the distal ends of the two rotary cutters 270c, 270d are separated from each other and are positioned away from each other, as shown in FIGS. 26A-26B and 26D-E. The first and second rotary cutters 270c, 270d in the first position may be positioned around tissue to receive tissue within a patient. The first and second rotary cutters 270c, 270d may be offset such that they do not cut or contact tissue when the jaw halves 208c, 208d are closed. The first and second rotary cutters 270c, 270d may similarly be rotated about the yaw axis 292 in the second position where the first and second rotary cutters 270c, 270d are configured to cut tissue within a patient when actuated, as shown in FIGS. 26C and 26F.

FIGS. 26A and 26D further illustrate the rotary cutters 270c, 270d in the first position, wherein the rotary cutters 270c, 270d are in an offset or stowed position, such as within the recesses 212 of each of the jaw halves 208c, 208d. FIGS. 26C and 26F illustrate the jaw halves 208c, 208d in the closed position, with the rotary cutters 270c, 270d in the second position. The rotary cutters 270c, 270d may be offset from the edge of the corresponding jaw halves 208c, 208d, such that the rotary cutters 270c, 270d can remain in the first position when the first and second jaw 208c, 208d are in the closed position. In the second position, the rotary cutters 270c, 270d are actuated and are rotated such that they are positioned closer together relative to one another and each rotary cutter 270c, 270d is positioned at least partially outside the recess 212 of the jaw halves 208c, 208d. In the second position, a cutting edge of each rotary cutter 270c, 270d may extend beyond the interior face 214 of each jaw half 208c, 208d. In the second position, the cutting edge of each rotary cutter 270c, 270d extends closer to a midline of the instrument 200 than in the first position.

The rotation of the rotary cutters 270c, 270d about a first axis causes the first and second jaw halves 208c, 208d, to rotate about the first axis until the face 214 of the first jaw half 208c contacts a face 214 of the second jaw half 208d. When the face 214 of the first jaw half 208c contacts the face 214 of the second jaw half 208d, further rotation of the rotary cutters 270c, 270d causes the rotary cutters 270c, 270d to move from the first position to the second position. As the rotary cutters 270c, 270d move from the first position to the second position, the rotary cutters 270c, 270d may cut tissue positioned between the first and second jaw halves 208c, 208d.

As best shown in FIGS. 26A-B and 26D-E, the surgical effector 208 may be controlled such that the first and second jaw halves 208c, 208d may be actuated to close first, without actuating the rotary cutters 270c, 270d. The rotary cutters 270c, 270d are offset such that the rotary cutters 270c, 270d are not actuated, such that they do not cut, when the first and second jaw halves 208c, 208d first close (as shown in FIGS. 26B and 26E). When the jaw halves 208c, 208d receive and grip the tissue, the electrodes may be activated for heating and cauterization of the tissue. As best shown in FIGS. 26C and 26F, after the jaw halves 208c, 208d have closed, the rotary cutters 270c, 270d can be actuated and deployed to cut the tissue. In some embodiments, the closing of the jaw halves 208c, 208d and the actuation of the rotary cutters 270c, 270d can advantageously be performed using the same actuation mechanism (e.g., one or more cables).

The rotation of the rotary cutters 270e about a first axis causes the first and second jaw halves 208c, 208d, to rotate about the first axis until the face 214 of the first jaw half 208c contacts the face 214 of the second jaw half 208d. When the face 214 of the first jaw half 208c contacts the face 214 of the second jaw half 208d, further rotation of the rotary cutters 270c, 270d causes the rotary cutters 270c, 270d to move from the first position to the second position.

The rotary cutters 270c, 270d may each be coupled to the first and second jaw halves 208c, 208d by one or more springs, such that the one or more springs may control or actuate the motion of the rotary cutters 270c, 270d.

As shown in FIGS. 24A-D, the rotary cutter 270c may be mechanically coupled to the jaw half 208c by a pin 228c. The pin 228c may be inserted into a hole 284c of the rotary cutter 270c, as shown in FIG. 25. As shown in FIGS. 24A-D, the pin 228c may be inserted into both the hole 284c of the rotary cutter 270c and into a hole 226c of the jaw half 208c to couple the jaw half 208c to the rotary cutter 270c.

A single actuation mechanism (e.g., one or more cables) can actuate both the jaw half 208c and its respective rotary cutter 270c. FIG. 26G illustrates a perspective view of a single jaw half and cutter of the second embodiment of the surgical effector shown in FIGS. 26A-F. From this view, one can see the connection of the pair of cable segments 230,232 that form a crimp 288c on the rotary cutter 270c. As best shown in FIGS. 24A-D, 25 and 26A-G, the rotary cutters 270c, 270d may have a groove or series of grooves 276 to receive and engage with cable segments. As the jaw half 208c and rotary cutter 270c are coupled, a single actuation element (e.g., the first and second cable segments 230, 232 as shown in FIGS. 26A-G) can actuate both the jaw half 208c and the rotary cutter 270c. The jaw half 208d and rotary cutter 270d may be similarly coupled and controlled by a single actuation element, such as another pair of cable segments. Each of the actuation elements can be used to close the jaw halves 208c, 208d and associated rotary cutter 270c, 270d.

The actuation element, such as the cable segments 230, 232, can be actuated such that the jaw half 208c will close first, followed by the rotary cutter 270c. As shown in FIGS. 24A-D and 26A-F, the separate actuation of the jaw half 208c and the rotary cutter 270c can be enabled by one or more mechanical springs 210c. The jaw half 208c can include one or more spring components 210c that also actuates the rotary cutter 270c. In the illustrated embodiment, the mechanical spring 210c is a torsion spiral spring. In other embodiments, the mechanical spring 210c may be a leaf spring, a series of Belleville washers, another type of torsion spring, a wave spring, or any other spring mechanism. The spring component 210c may allow the rotary cutter 270c to continue moving after the jaw half 208c is in the closed position. Once the jaw half 208c has been closed, the same actuation mechanism can continue to overcome the spring forces of the spring components 210c thereby causing the subsequent actuation of the rotary cutter 270c to move into the second position to cut tissue. Similar to the previous embodiments, advancing or retracting the cable segments 230, 232 causes the first jaw half 208c to rotate about the yaw axis 292, which allows the first jaw half 208c to move between the open and closed positions. The first and second cable segments 230, 232 may be advanced or retracted to rotate the jaw half 208c until the first jaw half 208c contacts the second jaw half 208d. Further tension in the spring component 210c can cause the rotary cutter 270c out of the slot 212 of the first jaw half 208c, which allows the rotary cutter 270c to move between the first and second positions. The spring component 210c allows the rotary cutter 270c to move relative to the jaw half 208c. The jaw half 208d and rotary cutter 270d may be include a similar spring component 210d and may be similarly actuated as the first jaw half 208c and rotary cutter 270c.

Once tissue cutting is complete, the actuation mechanism can be relieved of tension such that the spring component 210c (and thus the rotary cutter 270c) will spring back to its original offset position. As described previously, the actuation element can be the pair of cable segments 230, 232 that form a crimp 288c, as shown in FIG. 26G. As described previously, the spring components 210c, 210d are designed so that the jaw halves 208c, 208d may close at a certain pressure, without deploying the rotary cutter 270c, 270d. For example, the spring components 210c, 210d may be designed to close at a pressure of between about 0.5 kg/cm$^2$ to 15 kg/cm$^2$, such as between 3 kg/cm$^2$ to 10 kg/cm$^2$ onto tissue, without deploying the rotary cutters 270c, 270d. Note that any of the embodiments disclosed herein can utilize these spring components 210c, 210d to deploy and/or return the rotary cutters 270c, 270d to an offset or stowed position, in the first position.

Figure 27B:
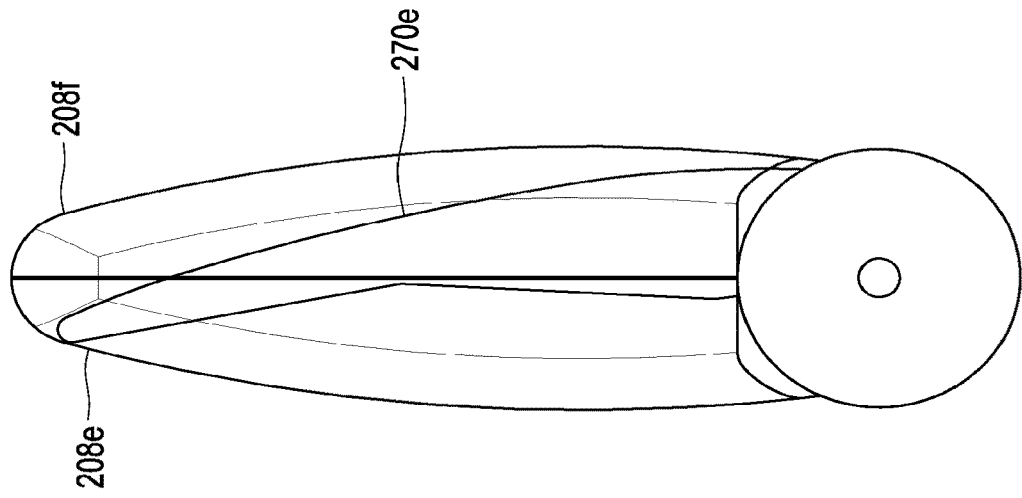
FIG. 27B illustrates a front view of the third embodiment of the surgical effector shown in FIG. 27A in a different position.
Figure 27A:
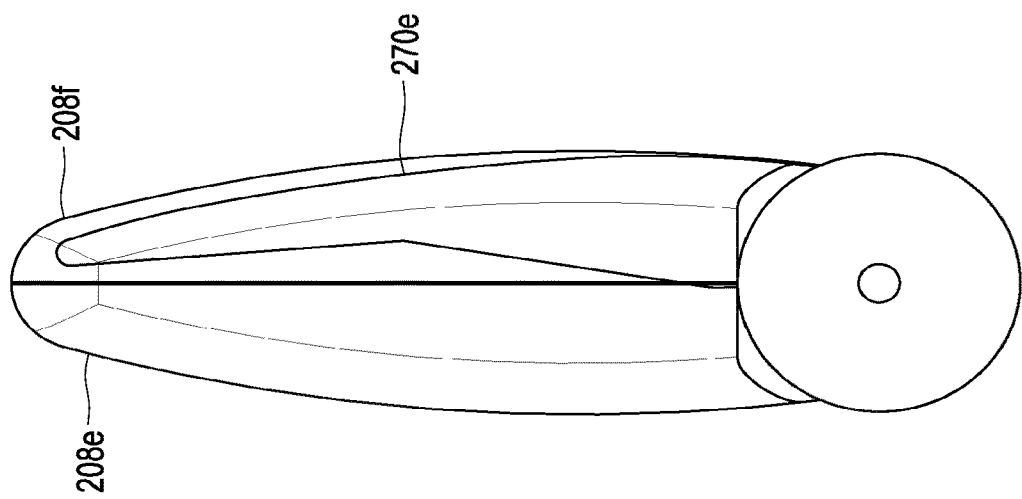
FIG. 27A illustrates a front view of a third embodiment of a surgical effector.

FIGS. 27A and 27B illustrate yet another embodiment of a surgical effector 208 including a rotary cutter; however, in the present embodiment, the surgical effector 208 includes a single blade rotary cutter, as opposed to a pair of blades or cutters. FIG. 27A illustrates a front view of another embodiment of the surgical effector 208, where the rotary cutter 270e is in the first position. The illustrated embodiment of the surgical effector 208 can be similar to the embodiments described previously, except with a single rotary cutter, instead of dual rotary cutters. In the first position, the rotary cutter 270e may be positioned in a recess of the second jaw half 208f. FIG. 27B illustrates a front view of the third embodiment of the surgical effector shown in FIG. 27A, where the rotary cutter 270e is in the second position. In the second position, the rotary cutter 270e may be deployed such that it is positioned at least partially outside the recess of the second jaw half 208f. In the second position, a cutting edge of the rotary cutter 270e may extend beyond the interior face 214 of the first jaw 208a and against or past the face 214 of the second jaw half 208b. In the second position, the cutting edge of the rotary cutter 270e extends closer to a midline of the instrument 200 than in the first position. The rotary cutter 270e may be offset from the edge of the corresponding jaw half 208e, such that the rotary cutter 270c can remain in the first position when the first and second jaw 208e, 208f are in the closed position.

In some embodiments, the rotary cutter 270e may be positioned at least partially in the first jaw half 208e in the second position. In some embodiments, the surgical effector 208 may be structured such that the rotary cutter 270e is positioned in the second jaw half 208f in the first position and at least partially positioned in the first jaw half 208e in the second position.

In some embodiments, the rotation of the rotary cutter 270e about a first axis causes one or more of first and second jaw halves 208e, 208f, to rotate about the first axis until the face 214 of the first jaw half 208e contacts a face 214 of the second jaw half 208f. When the face 214 of the first jaw half 208e contacts the face 214 of the second jaw half 208f, further rotation of the rotary cutters 270e causes the rotary cutter 270e to move from the first non-actuated position (shown in FIG. 27A) to the second actuated position (shown in FIG. 27B). As the single rotary cutter 270e moves from the first position to the second position, the rotary cutter 270e may cut tissue positioned between the first and second jaw halves 208e, 208f.

As in prior embodiments, the rotary cutter 270e may be coupled to the first jaw half 208e by one or more springs, such that the one or more springs may control or actuate the motion of the rotary cutter 270e, similar to the spring component described above in connection with the dual rotary cutters 270c, 270d, as shown in the second embodiment in FIGS. 24A-26G. The single rotary cutter 270e may rotate to cut tissue like a cleaver or scythe. In some embodiments, the single rotary cutter 270e can act as a guillotine.

The instrument 200 may include rotary cutters 270e or other type of cutting feature, such as scissors, arced scythe, razor, or blade and anvil, that can be deployed to cut tissue. The single rotary cutter 270e can be deployed to cut tissue in a rotary motion.

The first and second jaw halves 208e, 208f may be similarly structured and may also be similarly controlled as the first and second jaw halves of other embodiments disclosed herein. As described previously, the surgical effector 208 can act as a grasper or gripper. Similar to the first and second jaw halves of other embodiments described herein, the first and second jaw halves 208e, 208f may similarly rotate towards and away from each other to receive and grasp tissue.

As in prior embodiments, the jaw halves 208e, 208f are advantageously capable of first closing (e.g., to cauterize tissue), while maintaining the rotary cutter 270e in an offset or stowed position, such as within a slot or recess of the second jaw half 208f. Like the dual rotary cutters 270c, 270d, the single rotary cutter 270e can be initially offset such that the jaw halves 208e, 208f can first close (e.g., to cauterize tissue) without deploying the rotary cutter 270e.

In some embodiments, the surgical effector 208 can be designed such that the single rotary cutter 270e cuts against a fixed edge that is integral to the opposing second jaw half 208f.

FIG. 28A illustrates a front view of yet another embodiment of a surgical effector 208 that can include a cutter that is coupled to a linkage. FIG. 28B illustrates a front view of the fourth embodiment of the surgical effector 208 shown in FIG. 28A. FIG. 28C illustrates a front view of the fourth embodiment of the surgical effector 208 shown in FIGS. 28A-28B in another position.

The first and second jaw halves 208g, 208h may be similarly structured and may also be similarly controlled as the first and second jaw halves of the other embodiments as described herein. As described previously, the surgical effector 208 can act as a grasper or gripper. Similar to the first and second jaw halves of the other embodiments described herein, the first and second jaw halves 208g, 208h may similarly rotate towards and away from each other to receive and grasp tissue. FIG. 28A illustrates the surgical effector 208 with the first and second jaw halves 208g, 208h in the closed position. FIGS. 28B-28C illustrates the surgical effector 208 with the first and second jaw halves 208g, 208h in an open position.

In some embodiments, the instrument 200 can include a rotary cutter 270g that is coupled to a link. The rotary cutter 270g may also be referred to as a cutter, a blade, a cutting blade, a cutting element, or a cutting mechanism. As shown in FIGS. 28A-C, the surgical effector 208 includes the rotary cutter 270g that rotates to cut tissue like a cleaver or scythe. The rotary cutter 270g can be initially offset such that the jaw halves 208g, 208h can first close (e.g., to cauterize tissue) without deploying the rotary cutter 270g. As in other embodiments, the jaw halves 208g, 208h are capable of first closing (e.g., to cauterize tissue), while maintaining the rotary cutter 270g in an offset or stowed position, such as within a slot or recess of the first jaw half 208g.

Similar to previous embodiments described, the first and second jaw halves 208g, 208h may be similarly structured such that they also include one or more electrodes on the interior faces of the first and second jaw halves 208g, 208h. Sealing or cauterizing is accomplished via bipolar energy through the electrodes positioned on the interior faces of each jaw half 208g, 208h.

FIG. 28A illustrates the rotary cutter 270g in the first position. FIGS. 28B-28C illustrate the rotary cutter 270g in the second position. In the first position, the rotary cutter 270g may be positioned in a recess of the first jaw half 208g. In the second position, the rotary cutter 270g may be deployed such that it is positioned at least partially outside the recess of the first jaw half 208g. In some embodiments, the rotary cutter 270g may be positioned at least partially in the recess of the second jaw half 208h in the second position. In some embodiments, the surgical effector 208 may be structured such that the rotary cutter 270g is positioned in the first jaw half 208g in the first position and at least partially positioned in the second jaw half 208h in the second position.

The rotary cutter 270g may be offset from the edge of the jaw half 208g, such that the rotary cutter 270g can remain in the first position when the first and second jaw 208g, 208h are in the closed position. In the second position, a cutting edge of the rotary cutter 270g may extend beyond the interior face of each jaw half 208g, 208h. In the second position, the cutting edge of the rotary cutter 270g extends closer to a midline of the instrument 200 than in the first position. The rotation of the rotary cutter 270g about a first axis may cause the first and second jaw half 208g, 208dh, to rotate about the first axis until the face of the first jaw half 208g contacts a face 214 of the second jaw half 208h. When the face of the first jaw half 208g contacts the face of the second jaw half 208h, further rotation of the rotary cutters 270g causes the rotary cutter 270g to move from the first position to the second position.

As the single rotary cutter 270g moves from the first position to the second position, the rotary cutter 270g may cut tissue positioned between the first and second jaw halves 208g, 208h. The single rotary cutter 270g can be deployed to cut tissue in a relative rotational and/or translational motion. In some embodiments, the surgical effector 208 can be designed such that the single rotary cutter 270g cuts against a fixed edge that is integral to the opposing jaw half 208h.

Figure 29:
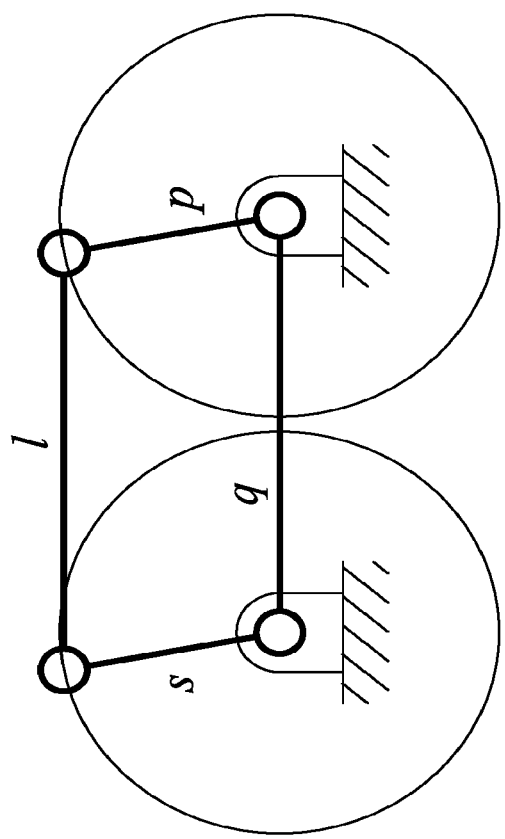
FIG. 29 illustrates the parallelogram linkage for continuous motion.

As shown in FIGS. 28A-C, a four-bar linkage is formed of four sides formed from the first jaw half 208g, the rotary cutter 270g and the pivot bars 296g, 298g. In some embodiments, the rotary cutter 270g may be coupled to the first jaw half 208g with pins in guiding slots. In some embodiments, the four-bar linkage may include a cable or belt constraint. The rotary cutter 270g may be coupled to one of the jaw halves 208g, 208h with the four-bar linkage to create a cutting path of motion, as shown in FIG. 29. FIG. 29 illustrates the parallelogram linkage for continuous motion. In some embodiments, the rotary cutter 270g may be coupled to the first jaw half 208g via pins through a first pivot bar 296g and a second pivot bar 298g that form a four-bar linkage. The four-bar linkage has four sides, having respective lengths of s, 1, p and q, which are shown in FIG. 29. In some embodiments, the portion of the first jaw half 208g has length of q, the first bar linkage 296g has a length of s, the portion of the rotary cutter 270g has a length of 1, and the second bar linkage 298g has a length of p. The portion of the first jaw half 208g may be the portion between the points where the first and second pivot bars 296g, 298g attach to the first jaw half 208g. The portion and length of the rotary cutter 270g may be the portion between the points where the first and second pivot bars 296g, 298g attach to the rotary cutter 270g.

The rotary cutter 270g may be controlled and actuated by the four-bar linkage or pivot. In some embodiments, the four-bar linkage results in a cutting path of motion that is curved or actuate, as shown in FIG. 29. The four-bar linkage provides the cutting motion wherein the cutting element simultaneously pushes against tissue and slices downward. This cutting motion is advantageously intended to optimize tissue cutting while minimizing dulling of the cutting blade, thereby allowing the instrument to be used multiple times in multiple procedures.

In the illustrated embodiment shown in FIGS. 28A-C, the rotary cutter 270g may be connected to the jaw half 208g to form the four-bar linkage in the form of a parallelogram. In some embodiments, the four-bar linkage forms the parallelogram linkage wherein opposing sides are equal in length, such as s+l=p+q. The four-bar linkage may create a path of motion where the rotary cutter 270g will move symmetrically and evenly such that a lower portion of the rotary cutter 270g will reach a cutting surface at generally the same time as an upper portion of the rotary cutter 270g. The rotary cutter 270g moves evenly and symmetrically relative to the cutting surface. In some embodiments, the cutting surface may be tissue received and gripped between the two jaw halves 208g, 208h. In this embodiment, the bottom portion of the rotary cutter 270g and the top portion of the rotary cutter 270g move together in alignment to cut the cutting surface, as shown in FIGS. 28B-C. The rotary cutter 270g may actuated along the cutting path motion by moving a rod coupled to the end of the rotary cutter 270g. In some embodiments, the rod may be moved in a proximal/distal and/or a sideways direction to actuate the rotary cutter 270g.

Figure 30C:
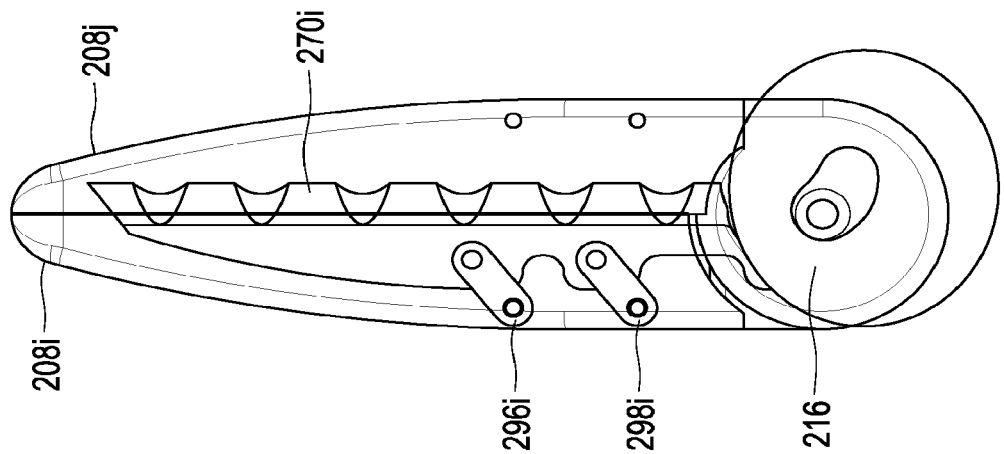
FIG. 30C illustrates a front view of the fifth embodiment of the surgical effector shown in FIG. 30A in a different position.
Figure 30B:
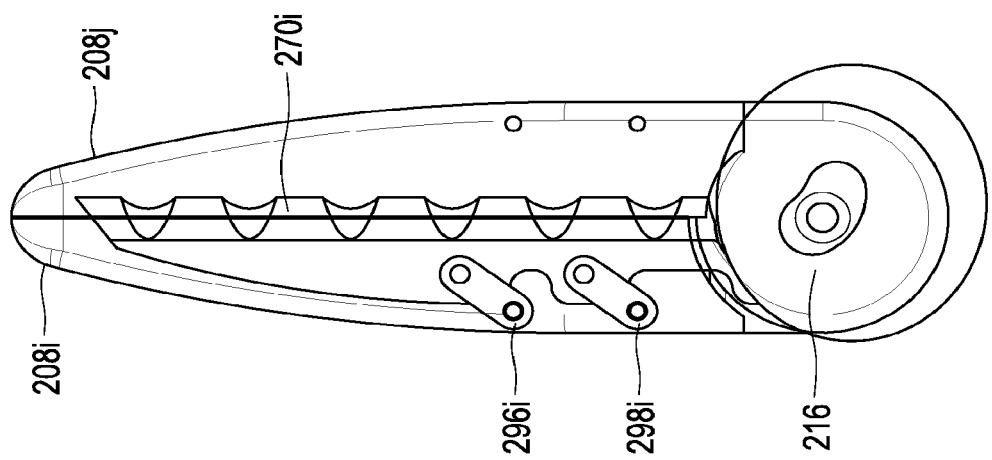
FIG. 30B illustrates a front view of the fifth embodiment of the surgical effector shown in FIG. 30A in a different position.
Figure 30A:
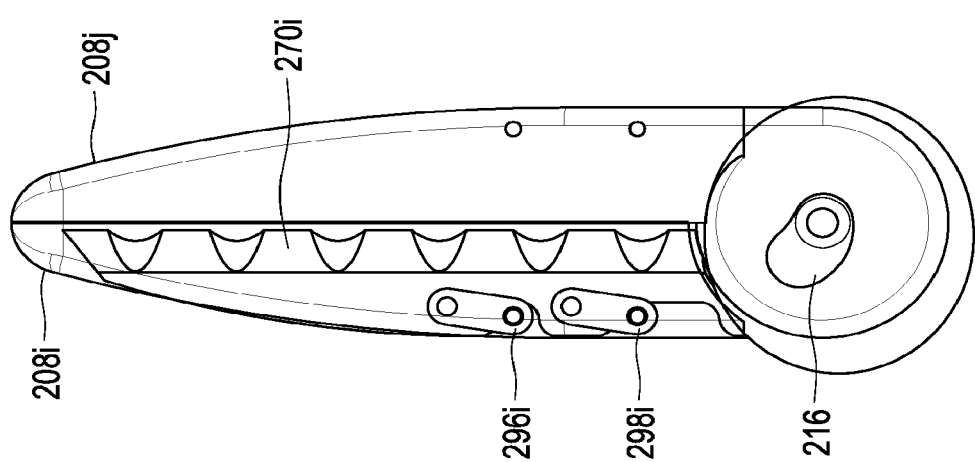
FIG. 30A illustrates a front view of a fifth embodiment of a surgical effector.

The embodiment illustrated in FIGS. 30A-C is similar to the embodiment shown in FIGS. 28A-C and described above, except with a non-parallelogram four-bar linkage, instead of the parallelogram four-bar linkage. By changing the dimensions of the four-bar linkage, one can advantageously fine tune the cutting element to make different types of cuts as desired. The dimensions (e.g. the lengths of s, l, p and q) can be changed by selecting pivot bars 296i, 298i of differing lengths and/or by changing the points at which the pivot bars 296i, 298i attach to the first jaw half 208i and the rotary cutters 270i. FIG. 30A illustrates a front view of a fifth embodiment of a surgical effector 208 with a rotational four-bar linkage blade or cutter 270i. FIG. 30B illustrates a front view of the fifth embodiment of the surgical effector 208 shown in FIG. 30A in a different position. FIG. 30C illustrates a front view of the fifth embodiment of the surgical effector 208 shown in FIGS. 30A-30B in another position.

As described previously, the surgical effector 208 can act as a grasper or gripper. Similar to the first and second jaw halves of the previous embodiments, the first and second jaw halves 208g, 208h of the fourth embodiment and the first and second jaw halves 208i, 208j of the fifth embodiment may similarly rotate towards and away from each other to receive and grasp tissue. FIGS. 30A-C illustrate the first and second jaw halves 208i, 208j in the closed position. FIG. 30A illustrates the rotary cutter 270i in the first position, offset and stowed in the recess of the first jaw half 208i. FIGS. 30B-C illustrates the rotary cutter 270i in the second position, where the rotary cutter 270i is positioned outside the recess of the first jaw half 208i and at least partially in the recess of the second jaw half 208j.

The rotary cutter 270i is connected to the first jaw half 208g with two pivot bars 296g, 298g to form of a four-bar linkage, which is not a parallelogram. In the embodiment shown in FIGS. 30A-C, the four-bar linkage is formed of opposing sides that may not be equal (e.g., wherein the length of p is greater than the length of s), such that it is a non-parallelogram linkage. In the embodiment shown in FIGS. 30A-C, the second pivot bar 298i is longer than the first pivot bar 296i. The rotary cutter 270i can move such that a first portion of the rotary cutter 270i (e.g., a lower portion) can reach a cutting surface before a second portion of the rotary cutter 270i (e.g., an upper portion), allowing higher pressures to be applied to tissue.

A first portion of the rotary cutter 270i (e.g., a lower portion of the blade) pivots/closes first, followed by a second portion of the rotary cutter 270i (e.g., an upper portion blade). The non-parallelogram four-bar linkage creates the rotary cutter 270i with an offset pivoting motion that can be customized. Even a minor difference in length of the first and second pivot bars 296i, 298i can help to create the rotary cutter 270i with an offset pivot, as shown in FIGS. 28B-C.

The instrument 200 may include a slot 216 formed in jaw halves 208i, 208j. The rotary cutter 270i may include a pin that is received in the slot 216. The slot 216 may be formed in the body of the first and second jaw halves 208i, 208j and/or the wrist 206 of the surgical instrument 200. The slot 216 may provide clearance for when the rotary cutter 270i is actuated or may be used as a bearing surface. The rotary cutter 270i may be actuated by moving the pin of the rotary cutter 270i within the slot 216. The pin mechanically coupled to the rotary cutter 270i may also be coupled to a rod. The rod may be moved in a proximal/distal and/or sideways direction to actuate the rotary cutter 270i.

Implementing Systems and Terminology.

Implementations disclosed herein provide system, methods, and apparatus for robotically enabled medical systems. Various implementations described herein include robotically enabled medical systems with a wrist comprising one or more pulleys shared by cable segments.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The robotic motion actuation functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A multi-functional surgical instrument, comprising:
   an elongate shaft extending between a proximal end and a distal end; a wrist extending from the distal end of the elongate shaft;
   an end effector extending from the wrist, the end effector comprising a first jaw and a second jaw, the first and second jaw being moveable between an open position in which ends of the jaws are separated from each other and a closed position in which the ends of the jaws are closer to each other as compared to the open position;
   a first rotary cutter extending from the wrist and positioned at least partially within a recess formed in a face of the first jaw; and
   the first and second rotary cutters are moveable between a first position in which ends of the first and second rotary cutters are separated from each other and a second position in which the ends of the first and second rotary cutters are closer to each other as compared to the first position; and
   wherein the first rotary cutter is offset from the face of the first jaw and the second rotary cutter is offset from the face of the second jaw, such that the first and second rotary cutters remain in the first position when the first and second jaw are in the closed position; and
   a second rotary cutter positioned in a recess formed in the second jaw.

2. The multi-functional surgical instrument of claim 1, wherein the first and second rotary cutters comprise a dual-blade scissor.

3. The multi-functional surgical instrument of claim 1, wherein the first rotary cutter is coupled to the first jaw by a first spring; and wherein the second rotary cutter is coupled to the second jaw by a second spring.

4. The multi-functional surgical instrument of claim 1, wherein the face of the first jaw engages tissue.

5. The multi-functional surgical instrument of claim 1, wherein the instrument further comprises a conducting material positioned on the face of the first jaw.

6. The multi-functional surgical instrument of claim 1, wherein the first rotary cutter is moveable between a first position in which a cutting edge of the first rotary cutter is recessed from the first jaw and a second position in which the cutting edge of the first rotary cutter extends beyond the face of the first jaw and against or past the face of the second jaw.

7. The multi-functional surgical instrument of claim 6, wherein the first rotary cutter is offset from the face of the first jaw, such that the first rotary cutter can remain in the first position when the first and second jaw are in the closed position.

8. The multi-functional surgical instrument of claim 6, wherein the motion of the first rotary cutter is coupled to the first jaw by a spring.

9. The multi-functional surgical instrument of claim 6, wherein rotation of the first rotary cutter about a first axis causes the first jaw to rotate about the first axis until the face of the first jaw contacts a face of the second jaw, and wherein upon the face of the first jaw contacting the face of the second jaw further rotation of the first rotary cutter causes the first rotary cutter to move from the first position to the second position.

10. The multi-functional surgical instrument of claim 6, wherein the first rotary cutter and the first jaw are actuated by a single actuation mechanism.

11. The multi-functional surgical instrument of claim 10, wherein the single actuation mechanism comprises one or more tension cables.

12. The multi-functional surgical instrument of claim 11,
   wherein the single actuation mechanism moves the first and second jaws between the open position and the closed position; and
   wherein the single actuation mechanism moves the first rotary cutter between the first position and the second position.

13. The multi-functional surgical instrument of claim 11,
   wherein the single actuation mechanism is first actuated to move the first and second jaws from the open position to the closed position; and
   wherein the single actuation mechanism is further actuated to move the first rotary cutter from the first position to the second position.

14. The multi-functional surgical instrument of claim 1, wherein the first rotary cutter is coupled to the first jaw.

15. The multi-functional surgical instrument of claim 1, wherein the first rotary cutter comprises a spring.

16. The multi-functional surgical instrument of claim 15, wherein the spring is a torsion spring.

* * * * *